(12) United States Patent
Rubinstein et al.

(10) Patent No.: US 6,365,713 B1
(45) Date of Patent: Apr. 2, 2002

(54) SOLUBLE LDL RECEPTOR, ITS PRODUCTION AND USE

(75) Inventors: Menachem Rubinstein, Givat Shmuel; Daniela Novick, Rehovot; Nathan Tal, Rehovot; Dina G. Fischer, Rehovot, all of (IL)

(73) Assignee: Yeda Research and Development Company, Limited, Rehovot (IL)

( * ) Notice: Subject to any disclaimer, the term of this patent is extended or adjusted under 35 U.S.C. 154(b) by 0 days.

(21) Appl. No.: 08/485,128

(22) Filed: Jun. 7, 1995

Related U.S. Application Data

(60) Division of application No. 08/092,817, filed on Jul. 19, 1993, now Pat. No. 5,496,926, which is a continuation-in-part of application No. 08/004,863, filed on Jan. 19, 1993, now abandoned.

(30) Foreign Application Priority Data

Jan. 19, 1992 (IL) ................................. 100696
Aug. 23, 1992 (IL) ................................. 102915

(51) Int. Cl.$^7$ ........................ C07K 14/00; C07K 1/00; A61K 38/16
(52) U.S. Cl. ........................ 530/350; 514/8; 530/412
(58) Field of Search ........................ 530/350; 514/8

(56) References Cited

U.S. PATENT DOCUMENTS

| | | | |
|---|---|---|---|
| 4,454,115 A | 6/1984 | Borden et al. | ................. 424/85 |
| 4,614,651 A | 9/1986 | Jarvis et al. | ................... 424/85 |
| 4,745,060 A | 5/1988 | Brown et al. | ............ 435/172.3 |
| 5,208,144 A | 5/1993 | Smith et al. | ..................... 435/6 |
| 5,521,071 A | * 5/1996 | Attie | ........................ 435/69.1 |

FOREIGN PATENT DOCUMENTS

| | | |
|---|---|---|
| EP | 0586094 | 7/1993 |
| WO | 94/01553 | 1/1994 |

OTHER PUBLICATIONS

Tolleshaug et al Cell vol. 32, 941–951 (1983).*
Remington's Pharmaceutical Sciences (Gennaro et al eds) (1990 18$^{th}$ Editon) pp. 821, 822, 817, 818.*
Van Driel et al J. Biol. Chem. (1989) vol. 264 (16): pp. 9533–9538.*
M Remmington's Pharmaceutical Sciences (1990) 18$^{th}$ ed. (Gennaro et al eds) pp. 817, 820, 821, 267, 268, and 1288 Philadelphia Coll. of Pharm & Science, Penn.*
Turini et al J. Pharm. & Exptl Thera. (1969) vol. 167, No. 1:pp. 98–104.*
Schneider et al Proc. Natl. Acad. Sci USA vol. 76 No.: 11 pp. 5577–5581 Nov. 1979.*
Yamamoto et al Cell vol. 39: pp. 27–38 Nov., 1984.*
Mikayama T. Molecular cloning and functional expression of a cDNA encoding glycosylation–inhibiting factor. Proc. Natl. Acad. Sci. USA vol. 90, pp. 10056–10060, 1993.*
Voet et al. Biochemistry, 1990. John Wiley & Sons, Inc., pp. 126–128 and 228–234.*
Duan, D–SR., et al. A Functional Soluble Extracellular Region of the Platelet–derived Growth Factor (PDGF) beta–Receptor Antagonizes PDGF–stimulated Responses. J. Biol. Chem. 1991. 266(1):413–418.*
Budavari, S. The Merck Index. Eleventh Edition. 1989. Merck & Co., Inc., p. 1070–1071, entry No. 6681.*
Judson, FN. In VItro Evaluations of Condoms with and without Nonoxynol–9 As Physical and Chemical Barriers Against Chlamydia Trachomatis, Herpes Simplex Virus Type 2, and Human Immunodeficiency Virus. Sexually Transmitted Diseases. 1989. 16(2):51–56.*
Van Driel, IR, Stoichiometric Binding of Low Density Lipoprotein (LDL) and Monoclonal Antibodies to LDL Receptors in a Solid Phase Assay. J. Biol. Chem. 1989. 264(16): 9533–9538.*
Kennett RH, et al. Monoclonal Antibodies. 1981. Plenum Press, New York, pp. 395–397.*
Duan et al., Journal of Biological Chemistry, 266. 413–418, Jan. 5, 1991.*
Spear et al, "Neutralization of Human Immunodeficiency Virus Type 1 by Complement Occurs by Viral Lysis", *J. Virology* 64(12):5869–5873 (1990).
Schneider et al., "Purification of the Low Density Lipoprotein Receptor, an Acidic Glycoprotein of 164,000 Molecular Weight", *J. Biological Chemistry* 257:2664–2773 (1982).
Weil et al., *Nature,* vol. p. 437, 1983.
Thomas et al., *Methods in Enzymology*, vol. 182, p. 499, 1990.

* cited by examiner

Primary Examiner—Prema Mertz
Assistant Examiner—Joseph F. Murphy
(74) *Attorney, Agent, or Firm*—Browdy and Neimark

(57) ABSTRACT

A soluble LDL receptor protein is provided. It can be isolated from cells that have been treated with an interferon, isolated from the urine of healthy human individuals or produced by recombinant techniques. The soluble LDL receptor protein is useful in protection of mammals against viral infections.

12 Claims, 19 Drawing Sheets

FIG. 1

| IFN, (U/ml) | 25 | 12 | 6.2 | 3.1 | 1.6 | .8 | .4 | .2 |
|---|---|---|---|---|---|---|---|---|
| NORMAL: | ● | ● | ● | ● | ● | ● | · | · |
| REMOVE: | ● | ● | ● | ● | · | · | | |
| REPLACE: | ● | ● | ● | ● | · | · | | |
| NEUTRALIZE: | ● | ● | ● | ● | · | · | | |

IFN-α

| NORMAL: | ● | ● | ● | ● | · | · | · | |
| REMOVE: | ● | ● | ● | · | · | | | |
| REPLACE: | ● | ● | ● | ● | · | | | |
| NEUTRALIZE: | ● | ● | ● | ● | · | · | | |

IFN-β

| NORMAL: | ● | ● | ● | ● | ● | · | · | · |
| REMOVE: | ● | ● | ● | · | · | | | |
| REPLACE: | ● | ● | ● | · | · | | | |
| NEUTRALIZE: | ● | ● | ● | ● | · | · | · | · |

IFN-γ

FIG. 10

| AAcid # | AAcid ID | R.Time (min) | C.Time (min) | Pmol (raw) | Pmol (-bkgd) | Pmol (+lag) | Pmol Ratio | AAcid ID |
|---|---|---|---|---|---|---|---|---|
| 1 | D | 5.43 | 5.58 | 16.70 | 12.03 | 13.23 | 53.94 | ASP |
| 2 | R | 15.62 | 15.62 | 6.52 | 3.83 | 4.25 | 12.16 | ARG |
| 3 | P | 19.73 | 19.68 | 6.66 | 1.58 | 2.11 | 4.26 | PRO |
| 4 | E | 9.35 | 9.50 | 12.53 | 5.10 | 6.74 | 14.78 | GLU |
| 5 | R | 15.67 | 15.62 | 4.91 | 2.40 | 3.13 | 8.95 | ARG |
| 6 | N | 6.17 | 6.27 | 8.89 | 6.71 | 8.33 | 17.43 | ASN |
| 7 | E | 9.35 | 9.50 | 11.22 | 4.47 | 5.78 | 12.67 | GLU |
| 8 | F | 25.07 | 25.00 | 7.34 | 5.57 | 7.38 | 32.77 | PHE |
| 9 | Q | 7.53 | 7.68 | 8.35 | 5.04 | 6.68 | 38.64 | GLN |
| 10 | | | | | | | | |
| 11 | Q | 7.52 | 7.68 | 5.18 | 1.93 | 2.37 | 13.01 | GLN |
| 12 | D | 5.43 | 5.58 | 7.10 | 3.42 | 5.31 | 21.65 | ASP |
| 13 | G | 8.65 | 8.80 | 14.84 | 2.66 | 3.43 | 3.31 | GLY |
| 14 | K | 26.20 | 26.13 | 2.63 | 0.79 | 0.79 | 2.14 | LYS |
| 15 | P | 19.70 | 19.68 | 5.03 | 1.46 | | 2.36 | PRO |

REPETITIVE YIELD ANALYSIS:

|  |  | Rep.Yield | Variance |
|---|---|---|---|
| D: | 1,12 | 89.21 % | :ASP 1.000 |
| R: | 2, 5 | 85.52 % | :ARG 1.000 |
| P: | 3,15 | 99.36 % | :PRO 1.000 |
| E: | 4, 7 | 95.67 % | :GLU 1.000 |
| Q: | 9,11 | 61.92 % | :GLN 1.000 |

Average AA Repetitive Yield     86.34 %

Combined AA Repetitive Yield     91.29 %     0.347

Theoretical Initial Yield:     6.67 pmol ( 13.35% )

FIG. 11

```
1 ..........................DRPERNEFQXQDGK.............. 14
                            ||.||||||||
1 MGPWGWKLRWTVALLLAAAGTAVGDRCERNEFQCQDGKCISYKWVCDGSA 50
```

FIG. 15A

```
     GCAGTGGGCGACAGATGTGAAAGAAAACGAGTTCCAGTGCCAAGACGGGAAATGCATCTCCTACAAGTGGGTCTGCGATGGCAGCGCTGAGTGCCAGGAT
     AlaValGlyAspArgCysGluArgAsnGluPheGlnCysGlnAspGlyLysCysIleSerTyrLysTrpValCysAspGlySerAlaGluCysGlnAsp
 1                              10                  20                  30
     TGCATTCCTCAGTTCTGGAGGTGCGATGGCCAAGTGCCAAGGCTCAGACGACGAGCAAGGCTGTCCCCCAAGACGTGCTCCCAGGACGAGTTT
     CysIleProGlnPheTrpArgCysAspGlyGlnValAspArgCysAsnGlySerAspGluGlnGlyCysProProLysThrCysSerGlnAspGluPhe
61                              70                  80                  90
     TCCTGCCCGGTGCTCACCTGTGTCCCCAGCTTCCAACACTGCCACTGTGGGCCTGGACAACGACCCCGACTGCGAA
     SerCysProValLeuThrCysGlyProAlaSerPheGlnCysAsnSerSerThrCysIleProGlnLeuTrpAlaCysAspAsnAspProAspCysGlu
121                             130                 140                 150
     TTCCACTGCCTAAGTGGGCAGTGCATCCACTCCAGCTGCCGTTAATGTGACACTCTGCCGAGGACACCAACAAGTTCAAGTGCCATCACCCTGGACAAA
     PheHisCysLeuSerGlyGluCysIleHisSerSerTrpArgCysArgCysAspLeuCysGluGlyProAspCysCysLysAspLysSerAspGluCysHisSerGlyGluCysIleThrLeuAspLys
181                             190                 200                 210
     AAGGACATGAGCGATGAAGTTGGCTGCGTTAATGTGACACTCTGCCGAGGACACCAACAAGTTCAAGTGCCATCACCCTGGACAAA
     LysAspMetSerAspGluValGlyCysValAsnValThrLeuCysGluGlyProAsnLysPheLysCysHisSerGlyGluCysIleThrLeuAspLys
241                             250                 260                 270
     AACGGCGGCTGTTCCCACGTCTGCAATGACCTTAAGATGGCTGGCTCTGCCCCAGCTGGCTTCCCAGCTGGTGGCCAGCAGGCTTCAGCCCAGATGCGAAGAT
     AsnGlyGlyCysSerHisValCysAsnAspLeuLysLysIleGlyTyrGluCysLeuCysProAspGlyPheLeuValAlaAlaGlnArgArgCysGluAsp
301                             310                 320                 330
     GGCTTCCAGCTGGACCCCACACACGAAGCCCTGTGTGGGCCCTACCTCTTCTTCACCAACCGGCACGAGGTCAGGAAGATGACGCTG
     GlyPheGlnLeuAspProHisThrLysAlaCysLysAlaLysIleAlaTyrLeuPhePheThrAsnArgHisGluValArgLysMetThrLeu
361                             370                 380                 390
     TACTGGTCTGACCTGTCCCAGAGAATGATCTGCAGAGAGCCCACGGCCGTCTTCTTCTATGACACCGTCATCAGCAGGGACATCCAG
     TyrTrpSerAspLeuSerGlnArgMetIleCysSerThrGlnLeuLeuAspArgAlaHisGlyValSerSerTyrAspThrValIleSerArgAspIleGln
```

```
  -13    1
AGAGGCTGCGAGCATGGGGCCCTGGGGCTGGAAATTGCGCTGGACCGTGCCCTTGCTCCTCCGCCGGGGGGACT    63
           MetGlyProTrpGlyThrValArgTrpLysLeuArgTrpThrValAlaLeuLeuAlaAlaGlyThr
                -20                 -10                              -1

GGCTCTGATGAGTCCCAGGAGACGTGCTTGTCTGTCTGCTTCACCTGCAAATCCGGGACTTCAGCTGTGGGGGCCCTGTCAACCGC    243
GlySerAspGluSerGlnGluThrCysLeuSerValSerLeuHisLysSerGlyPheSerCysGlyGlyArgValAsnArg
             20                  30                  40                  50                  60

CGCTCCACGATGGGAAGTGCCATCTCTCGGCAGTTCGTCTGCTGACTCAGACCGGACTTCTGACGGCTCAGACGAGCC    423
ArgCysHisAspGlyLysCysIleSerArgGlnPheValCysAspSerAspArgArgAspCysLeuAspSerAspGluAla
        70                   80                  90                 100                 110                 120

GATGGCTCGGATGAGTGCCGCAGCGCTGAGGGTCTTTACGTGTTCCAAGGGACAGTAGCCCCTGCTCGGCCTTCGAG    603
AspGlySerAspGluTrpProGlnArgCysArgGlyLeuTyrValPheGlnGlyAspSerSerProCysSerAlaPheGlu
               130                 140                 150                 160                 170                 180

ACCTGCTCGCCCCTGACGAATTCCAGTGCTCTGATGGAAACTCCATGCCAGCCGGCAGTGACCGGAATATGACTGC    783
ThrCysArgProAspGluPheGlnCysSerAspGlyAsnCysIleHisGlySerArgGlnCysAspArgGluTyrAspCys
           190                 200                 210                 220                 230                 240

GTCTGCAACATGGCTAGAGACTCGGGACTGCTGGTCAGAGATGAACCTCAAAGAGTGCGGGACCAACGAATGCTTGGACAAC    963
ValCysAsnMetAlaArgAspCysArgAspTrpSerAspGluProIleLysGluCysGlyThrAsnGluCysLeuAspAsn
              250                 260                 270                 280                 290                 300

ATCGATGAGTGTCAGGATGACCCGACACCTGCAGCCCGACACCTGAACCTGCGTGAACCTGGCTACAAGTGCCAGTGTGAGGAA    1143
IleAspGluCysGlnAspProAspThrCysSerGlnLeuCysValAsnLeuGlyGlyTyrLysCysGlnCysGluGlu
             310                 320                 330                 340                 350                 360

GACCGGAGCGAGTACACACCAGCCTCATCCCCAACCTGAGGAACGTGGTCGCTCTGGACGAAGTGGCCAGCACGGAGAATC    1323
AspArgSerGluTyrThrProAlaSerSerProAsnLeuArgAsnValValAlaLeuAspThrGluValAlaSerAsnArgIle
              370                 380                 390                 400                 410                 420

GCCCCGACGGCCTGGCTGTGGAGATCGGTGGACACTCTGACCGACTCTGTCCTCCTCTGTTGCG    1503
AlaProAspGlyLeuAlaValAspTrpIleHisSerAsnIleTyrTrpAspThrSerValLeuGlyThrValSerValAla
             430                 440                 450                 460                 470                 480

GACTGGGGAACTCCCGCAAGATCAAGAAAGGGCCTGAATGCTGTGGACATCTACTGCTGACTGTGACATTCAG    1683
AspTrpGlyThrProAlaLysIleLysLysGlyLeuGlyLeuAsnGlyValAspIleTyrSerLeuValThrGluAsnIleGln
```

```
     430                    440                    450
421  GATACCAAGGGCGTGAAGAGGAAAACGTTATTCAGGGAGAACGGCTCCAAGCCAAGGGCCATCGTGGTGGATCCTGTTGATCCTGTTCATGGCTTCATGTACTGGACT
     AspThrLysGlyValLysArgLysThrLeuPheArgGluAsnGlySerLysProArgAlaIleValAlaAspProValHisGlyPheMetTyrTrpThr 490                    500                    510
481  TGGCCCAATGGCATCACCCTAGATCTCCTCAGTGGCCGCCCTCTACTGGGTTGACTCCAAACTTCACTCACTCCAAACTTCAAGCATCGATGTCAATGGGGCAAC
     TrpProAsnGlyIleThrLeuAspLeuLeuSerGlyArgLeuTyrTrpValAspSerLysHisSerIleSerSerIleAspValAsnGlyGlyAsn 550                    560                    570
541  GATATCATCAACGAAGCCATTTTCAGTGCCAACGACGTTGTTGGCTGATGTCAACTTGTTGGCTGAAAAACTACTGTCCCAGAGGATATGGTCCTC
     AspIleIleAsnGluAlaIlePheSerAlaAsnArgLeuThrGlySerAspValAsnLeuLeuAlaGluAsnLeuLeuSerProGluAspMetValLeu 610                    620                    630
601  CTCCCTGCCCAGATCAACCTCACTGCCCAAGTTACCTGC(Cys)GCCTGCCCGGACGGCAATGGAGCTGCCCTCACAGAG    FIG.15D
     LeuProAlaProGlnIleAsnProHisSerProLysPheThrCysAlaCysProAspGlyMetLeuLeuAlaArgAspMetArgSer(Cys)LeuThrGlu 670                    680                    690
661  ACCACCCGGCCTGTTCCCGACACCTCCCGGCTCACCACGGTGGAGATAGTGACAATGTCTCACCAAGCTCTGGGCGAC
     ThrThrArgProValProAspThrSerArgLeuProGlyAlaThrThrValGluIleValThrMetSerHisGlnAlaLeuGlyAsp
        721  ......         730                    740                    750
721  CTTTGCCTGGGGGTCTTCCTTTCTATGGAAGAACTGGCGGCTTAAGAACATCAACAGCATCAACTTTGACAACCCCGTCTATCAGAAGACCACAGAGGAT
     LeuCysLeuGlyValPheLeuLeuValTrpLysAsnTrpArgLeuLeuLysAsnIleAsnPheAspAsnProValTyrGlnLysThrThrGluAsp 790                    800                    810
781  ACATCTGCCCTGGAGTCCCGCCCCTGCCCCAGAACCCTTCCTGAGACCTCGCGGCCCTTGTTTATTCAAAGACAGAAGACCAAAGCATTGCCTGCCAG

TGGTTTCTTCCTTCCTGTGAAGAGATAAGAAACAGGCCCGGGGACCAGGATGACACCTCCATTCTCTCCAGGAAGTTTTGAGTTTCTCTCCACC

GCAGATGCACCAACGGGACCCCCTGGCCCTGCCTCATCCACCAAATCTCTAAGCCAAATCCAGGAGTCAACGTGTTTACCTCTCTATGCA

TACCTTCCTTAAGCCAGGAAAGGGATTCATGGCGTCGAATGATCTGGAAATCCGTGGTGGCACCGAGACCGAGAACTCATTCACCAAATGATGCCAC
```

```
                520         530         540
CGGAAGAGACCATCTTGGAGGATGAAAAGAGGCTGGCCACCCCTTCTCCTTTGGCCGTCTCTTTGAGGACAAAGTATTTTGGACA    1863
ArgLysThrIleLeuGluAspGluLysArgLeuAlaThrProPheSerLeuAlaValHisProPheGluValPheLysAspLysTyrPheGlyThr
    580         590         600
TTCCACAACCTCACCCAGCCAAGGAGGAGTGAACTGGTGTGAGAGGACCACCCTGAGACAAATGGCGGCTGCCAGTATCTGTGC    2043
PheHisAsnLeuThrGlnProArgGlyValAsnTrpCysGluArgThrThrLeuArgSerAsnGlyGlyGlnTyrLeuCys
    640         650         660
GCTGAGGCTGCAGTGGCCACCCAGGAGACATCCAGGTCAGCTCAGGCCGTAAGGTGACGCCGTAAAGGACACAGCACACA    2223
AlaGluAlaAlaValAlaAlaThrGlnGluThrSerArgSerAlaArgLeuLysLysValSerSerThrAlaValArgThrGlnHisThr
    700         710         720
GTTGCTGGCAGAGGAAATGAGAGGAAGCCCAGTAGCCGTGAGGGCTCTGTCCATTGTCCTCCCCATCGTGCTCCTCGTCTTC    2403
ValAlaGlyArgGlyAsnGluGluLysProSerSerValArgAlaLeuSerIleValLeuProIleValLeuLeuValPhe
    760         770         780
GAGGTCCACATTTGCCACAACCAGGACGGCTACAGCTACCCCTCGAGACAGATGGTCAGTCTGGAGATGACGTGGCGTGA    2583
GluValHisIleCysHisAsnGlnAspGlyTyrSerTyrProSerArgGlnMetValSerLeuGluAspValAla***
    820         830
AGCTTTGTTTTATATATTTATTCATCTGGGAGGCAGAACAGGCTTCGGACAGTGCCCATGCAATGGCTTGGGTTGGATTT    2763

GTGACACAATCCTCAAACATGGAAGATGAAAGGGCAGGGGATGTCAGGCCCAGTGTTGCCCTGTCACCCCGAATCATGACCCAGTGTCTTTCGAGGTGGGTTTG    2943

AGCCTTGCTAGACAGCAGAGCCTGAGTCACCGGTTCACCGGTCACTGTAGTACATTTGGCATTTGTGTTATTATTTGCACTGTTTTCTGTCGTGTGTTGGGAT    3123

TTCCAGAGGCAGAGCCTGAGTCACCGGTTCACCGGTTCACCTGGAGACACCCGGTTACCTTGGCCGTGAG    3303

TCTCAGTTCAGAGTTGTCTCTTTATGTCCGCCCACCTGTGTACATTTGTCTTCCACTGTTTCTGTCGTGTGTTGGGAT    3483

TGCCATTGTCGTCTTTATGTCCGCCCACCTAGTGCTCTTCCAAGCCATTCACTTCCCAATCT    3663

TCATGAGGTCAGGAGATCGAGACCATCCTGGGGCTAACAAGGTGAAACCCGTCTCTCTACTAAAAATACAAAAAATTAGCCGGG    3843

CACTCGAGTCCGCAGTGTCTGGCCTGGGCGACAGAGCGAGACTCCGTCTCAAAAAAAACAAAACAAAAAAAAAAACCATGCATGG    4023
```

GACACGTGGCCTGCACCCAGGTGTGGCTGTCAGGACACCAGCCTGTGCCCATCCTCCCGACCCTACCCACTTCCATTCCCGTGTCTCCTTGCACTT
GGGATCCCAGGCCAGGGAAAGCCCGTGTCAATGAATGCCCGGGGACAGAGAGGGACAGGTTGACCGGGACTTCAAAGCCGTGATCGTGAATATCGAGAAC
TGTCGTTGATGGGTATGTGTTTAAAACATGCACGGTGAGGCCCAGTGCCCTCACGCCTGTAATCCCAGCACTTTGGGAGGCCGAGGCGGGTGGA
CGCGGTGGTGGGCACCTGTAGTCCCAGCTACTCGGGAGGCTGAGGCAGGAGAATGGTGTGAACCCGGGAAGCGGAGCTTGCAGTGAGCCGAGATTGCGC
TGCATCAGCAGCCCATGGCCTCTGGCCAGGCATGGCGAGGCTGAGGTGGGAGGATGGTTTGAGCTGTCAGGCATTTGAGGCTGTCGTGAGCTATGATTATG
TGTAATCCCAGCACTTGGGAGGCTGAGCTGATCACTTGAGTTCAGTGAGTTGGAGACCAGGCCTGAGCAACAAGCGAGATCCCATCTCTACAAAAAC
TGAGCCCAGGAGGTGGAGGTTGCAGTGAGCCAATGATGAGCCACTGCACTCCAGCCTGGGCAACAGAGATGAAGACCCTATTTCAGAAATACAACTATAAA
ATGTCCGGAGAGACAGTGACAGCCCTCCGTCAGACTCCCCGTCGAAGATGTCACAAGGGACAAAACACTGTGTCCCCCC
TGTTTGCACTTTGTATATTGGTTGAAACTGTCACTTATCACTTATATATATATATAAATCTATTATTTTGCAAACCCTGGTTGCTG
TTTGCACGAACTGGACTGTGTGCAACGCTTTTTTGGGAGAATGATGTCCCCGTTGTATGTATGAGTGGCTTCTCGGGAGATGGGTGTCACTTTTTAAACCA

FIG. 15F

```
CCACTGCTTTCCAGCCTGGGCAACATAGTAAGACCCCATCTCTTAAAAAATGAATTTGGCCAGACACAGGTGCCTCACGCC    4203
CAAAAAGTTAAAAATCAGCTGGGTATGGTGGCACGTGCCTGTGATCCCAGCTACTTGGGAGGCTGAGGCAGGAGGATCGCC    4383
AAAAATAAAATAAAATCCCTCCAGTCTGACGGGACTTCAGGTTCTTTCTGAAATCGCCGTGTTACTGTTGCACTG    4563
AGTGCAGGGAACCGTGATAAGCCTTTCTGGTTTCGGAGCACGTAAATGCGTCCCTGTACAGATAGTGGGATTTTTGTTA    4743
TATTTGTTCAGTGACTATTCTCGGGCCCTGTGTAGGGGTTATGCCCTCTGAAATGCCTCTTCTTTATGTACAAAGATTA    4923
CTGTATAGAAGGTTTTTGTAGCCTGAATGTCTTACTGTGATCAATTAAATTTCTTAAATGAAAAAAAAAAA$_N$    5103
```

FIG. 19

```
MGPWGWKLRWTVALLLAAAGTAVGDRCERNEFQCQDGKCISYKWVCDGSA......Pre-LDLR
                      ||| ||||||| ||||  |||
                      DRXERNEFQXQDGK XI..................sLDLR
1.........10.........20.........30.........40.........50
```

SOLUBLE LDL RECEPTOR, ITS PRODUCTION AND USE

The present application is a divisional of U.S. application Ser. No. 08/092,817, filed Jul. 19, 1993, now U.S. Pat. No. 5,496,926, which is a continuation-in-part of U.S. application Ser. No. 08/004,863, filed Jan. 19, 1993, now abandoned, the entire contents of which are hereby incorporated herein by reference.

BACKGROUND OF THE INVENTION

1. Field of the Invention

The present invention relates to the soluble low density lipoprotein (LDL) receptor, to its production and to pharmaceutical compositions containing it.

2. Description of the Background Art

Interferons (IFN) are inducible proteins that are produced by various cells and induce an antiviral state in animal cells. There are three major types of IFNs, distinguished by their antigenic properties: α, β and γ. IFN-α and IFN-β are related proteins of 166 or 165 amino acid residues that are induced by viruses or nucleic acids and are produced by cells from various tissues, including immune cells. IFN-γ is a protein of 130–143 amino acid residues which is produced by mitogen-activated T-cells and by large granular lymphocytes. The production of IFN is usually transient and it stops shortly after the inducer disappears. For a recent review of these issues, see Taylor S. L. and Grossberg S. E., 1990, Virus Research, 15, 1–26.

In addition to the three well-characterized types of interferons, there are several reports describing partially characterized species of interferons. A group of IFN-α-like (IFN-α1) genes and pseudogenes, also known as class II IFN-α or IFN-omega was discovered and reported (Revel, M., 1984, in "Antiviral Drugs and Interferon: The Molecular Basis of their Activity", Y. Becker (ed.), Martinus Neijhoff Publ., Boston, pp. 357–434; Capon, D. J. et al., 1985, Molec. Cell. Biol., 5, 768–779; Hauptmann, R. and Swetly, P., 1985, Nuc. Acid. Res., 13, 4739–4749). These are virus-induced interferons having about 172 amino acid residues which are present in the natural mixture of human IFN-α produced by leukocytes (Adolf, G. R., 1990, Virology, 175, 410–417).

Treatment of human peripheral blood mononuclear leukocytes with a mitogen resulted in production of IFN-γ and a novel IFN-like substance named IFN-δ (Wilkinson, M. and Morris, A., 1983, Biochem. Biophys. Res. Comm. 111, 498–503). IFN-δ was found to be acid resistant and active only on human fibroblasts having chromosome-21 trisomy and not on WISH cells. It was antigenically distinct from the three known IFN types.

Acid-labile alpha-interferons were described in several publications. An acid-labile IFN-α was induced in cultures of lymphocytes from individuals who have recently received influenza vaccine, by stimulation in vitro with the influenza virus (Balkwill, F. R. et al, 1983, J. Exp. Med., 157, 1059–1063). This type of IFN was neutralized by anti-IFN-α serum and was active on Mandin Darby Bovine Kidney (MDBK) cells. The presence of such acid-labile alpha-type IFN in sera of patients with systemic lupus erythematosus was reported (Klippel, J. H. et al, 1985, Annals Rheum. Disease, 44, 104–108). An acid-labile IFN-α was produced similarly to IFN-α by Sendai virus induction of human peripheral leukocytes (Matsuoka, H. et al., 1985, J. Gen. Virol., 66, 2491–2494). Acid-labile IFN-α was spontaneously produced in cultures of peripheral blood mononuclear cells (Fischer, D. G. and Rubinstein, M., 1983, Cellular Immunology, 81, 426–434).

Another type of IFN, called IFN-epsilon, was produced by epithelial cells exposed to virus. It was produced together with IFN-β but was active on epithelial cells and not on other cell types (Jarvis, A. P. and Kosowsky, D. I., 1984, U.S. Pat. No. 4,614,651).

Among other cytokines, TNF, IL-6 and IL-1 were reported to exhibit antiviral activity (Mestan, J. et al., 1986, Nature, 323, 816–819; Wong, G. H. W. and Goedell, D., 1986, Nature, 323, 819–822; Billiau, A., 1987, Antiviral Research, 8, 55–70). TNF is produced only by immune cells and it was suggested that IL-1 and TNF exert their antiviral activity by inducing the production of IFN-β (Billiau, A., op.cit.).

Several interferon-induced proteins have been identified and some of them were shown to be instrumental in the induction of the antiviral state by IFNs. The best studied one is (2'-5') oligo adenylate synthetase, an intracellular enzyme which polymerizes ATP into pp(A2'-5'p)nA, where n is preferably 2 or 3, but may be as long as 15 (Kerr, I. M. and Brown, R. E., 1978, Proc. Natl. Acad. Sci. USA, 75, 256–260). Such oligomers activate a latent ribonuclease (RNASE-F) which degrades ribosomal RNA and polysomes, thereby inhibiting viral and cellular protein synthesis. Another IFN-induced intracellular enzyme is a 2'-5'; phosphodiesterase which may remove the CCA terminus of tRNA, thereby leading to inhibition of protein synthesis (Schmidt, A. et al., 1979, Proc. Natl. Acad. Sci. USA, 76, 4788–4792). A third known IFN-induced intracellular enzyme is a 70 Kd protein kinase which phosphorylates the Initiation Factor eIF-2, thereby leading to inhibition of the initiation of mRNA translation into proteins (Ohtsuki, K. et al., 1980, Nature, 287, 65–67).

Other IFN-induced intracellular proteins include the nuclear IFN-Responsive Factors (IRF-1 and IRF-2) which regulate IFN-responsive genes; metallothioneis, a 56 Kd protein of unknown function in the IFN-induced antiviral state; Factor B of the alternative complement system and the murine Mx gene product, which is responsible for resistance to influenza (Reviewed in Taylor, I. L. and Grossberg, S. E., 1990, Virus Research, 15, 1–26). Other IFN-induced cell associated polypeptides were identified on 2-D gels following IFN treatment and [$^{35}$S]-methionine pulsing, but these proteins were not further characterized in terms of their structure and function (Weil, J. et al., 1983, Nature, 301, 437–439). Several cell surface interferon-induced proteins were identified, including class I and II MHC antigens, IgG, Fc receptor and cytoskeletal components (Reviewed in Revel, M., 1984, in "Antiviral Drugs and Interferons: The Molecular Basis of their Activity", Y. Becker (ed.), pp. 357–434, Martinus Neijhoff Publ., Boston).

Additional IFN-induced proteins that were secreted into the medium have been disclosed in the literature, such as β2-microglobulin, a shedded component of the cell-surface class I MHC antigens (Dolei, A. F. et al., 1981, Antiviral Res., 1, 367–373), and plasminogen activator and lymphotoxin, which were induced in lymphocytes by IFN (Jones, C. M. et al., 1982, J. Interferon Res., 2, 377–386; Wallach, D. and Hahn, T., 1983, Cellular Immunol., 76, 390–396). IFN-γ-treated monocytes released TNF which enhanced the overall antiviral effect (Gerrard, T. et al., 1989, J. Interferon Res., 9, 115–124). IFN-γ-induced proteins of molecular weight 30,000 (extracellular) and 25,000 (intracellular) were described (Luster A. D. et al., 1988, J. Biol. Chem., 263, 12036–12043), but their role was not determined.

Although many IFN-induced proteins have been disclosed, none of them is related to a soluble LDL receptor.

The existence of a soluble LDL receptor as a separate protein has not been so far disclosed. The full size low density lipoprotein receptor (LDLR) is a transmembrane glycoprotein which is not soluble in the absence of detergents. It consists of 839 amino acid residues and exhibits a molecular weight of 164,000. Its only known function is to internalize LDL and VLDL. Structurally it consists of several domains, some of which are shared with other proteins. The N-terminal ligand-binding domain is made of 292 amino acid residues arranged in 7 cysteine-rich imperfect repeats. This domain is followed by a region homologous to the EGF precursor (400 amino acid residues), a region of 58 amino acid residues rich in O-linked sugars, a single transmembrane domain of 22 amino acid residues and a cytoplasmic domain of 50 amino acid residues (Schneider W. J. et al., J. Biol. Chem. 257, 2664–2673, 1982; Yamamoto T. et al., Cell 39, 27–38, 1984). However, there is no mention of antiviral properties of the LDL receptor. The predicted nucleotide sequence (SEQ ID NO:3) of the cDNA corresponding to the LDL receptor in the mRNA, including the predicted LDL receptor amino acid sequence (SEQ ID NO:4) encoded thereby, according to Yamamoto et al (supra) is presented in FIG. 15.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

It has been found that when human fibroblasts or epithelial cells are treated with an interferon, a protein showing antiviral activity is produced and accumulates in the supernatant of the cell cultures. This protein has now been purified to homogeneity and was identified as the soluble extracellular region of LDL receptor.

The present invention thus provides a soluble LDL new receptor protein consisting essentially of at least one replication of the soluble portion of an LDL receptor, or a mutein, fused protein, salt, functional derivative and/or active fraction thereof. The antiviral activity of the receptor protein may be conveniently determined, for example, in a system consisting of WISH amino cells and vesicular stomatitis virus (VSV) as a challenge.

The invention also provides a soluble LDL receptor corresponding to the extracellular portion (750 amino acid residues) of the LDL receptor, which is purified to homogeneity with respect to proteinaceous impurities.

The invention relates especially to the soluble LDL receptor comprising at least, but not exclusively, the ligand binding domain of the mature LDL receptor, and, more specifically, corresponding at least to amino acid residue 4 to 292–350 of SEQ ID NO:4 or any range therein, such as at about amino acid residue 313 of the mature LDL receptor, corresponding to 25 amino acid residues to 313–371, of SEQ ID NO:4 or any range therein, such as amino acid residues 25–313 of the LDLR precursor sequence. The C-terminus of a soluble LDL receptor is expected to be between amino acids 292 and 350 of the mature LDL receptor protein, or 313–371 of the LDLR precursor, such as any value therein.

The invention also relates to a soluble LDL receptor, including the amino acid sequence substantially as shown in FIG. 10.

In another aspect, the invention relates to a process for the preparation of the soluble LDL receptor, comprising treatment of suitable cells with an interferon, isolation of the soluble LDL receptor from the supernatant and purification thereof.

The invention further concerns recombinant DNA molecules comprising the nucleotide sequence coding for said protein or for its active muteins or fused proteins, expression vehicles comprising them and host cells transformed therewith and to a process for producing the soluble LDL receptor, its active muteins or fused proteins, by culturing said transformant cells in a suitable culture medium.

The soluble LDL receptor of the invention, its active muteins, fused proteins, and their salts, functional derivatives and active fractions, are for use as active ingredients of pharmaceutical compositions to protect mammals against viral infections.

The present invention also relates to methods for treating cells in mammals against viral infection by administration of an anti-viral effective amount of a pharmaceutical composition comprising a soluble LDL receptor protein of the present invention.

The present invention also relates to naturally occurring soluble LDL receptor. Such soluble LDL receptors can be purified and/or isolated from biological fluid samples, such as urine.

The invention also relates to methods for purifying soluble LDL receptor from biological fluid samples comprising isolation and/or purification of soluble LDL receptors from concentrated and/or filtered biological samples containing a soluble LDL receptor.

BRIEF DESCRIPTION OF THE FIGURES

FIG. 1 shows evidence for the existence of antiviral activity which is not the added interferon. The protective effect of various interferons against the cytopathic effect of vesicular stomatitis virus (VSV) on human amino WISH cells, is determined under a variety of conditions. The assay was performed in 96-well plates and each row represents a serial two-fold dilution of IPN. The final concentration of IFN in the first column from left is 25 IU/ml. From top: Row 1: IFN-α added and VSV added after 24 hrs; Row 2; IFN-α added, cells washed after 24 hours, fresh IFN-α added and VSV added; Row 3: IFN-α added, neutralizing anti-IFN-α antibody added after 24 hrs, followed by addition of VSV. Rows 4 to 6 and 7 to 9 are replicates of the first three rows, except that IFN-β and anti-IFN-β antibody, and IFN-γ and anti-IFNγ antibody were used, respectively.

FIG. 10 shows the original output of the protein microsequencer. Fractions 10–12 of RP-HPLC (FIG. 7) 0.4 ml each, were pooled, concentrated by ultrafiltration and the resulting sample (1 μg) was subjected to protein microsequence analysis. The N-terminal 15 amino acid residues (SEQ ID NO:1) found in this manner are shown.

FIG. 11 shows the computer output of the search for the sequence obtained by the protein microsequencer shown in FIG. 10. Amino acids 1–14 of SEQ ID NO:1 are compared to the N-terminal 50 amino acids of the human LDL receptor (SEQ ID NO:2).

FIGS. 15A–15F shows the nucleotide sequence (SEQ ID NO:3) of the cDNA corresponding to the LDL receptor mRNA and the predicted amino acid sequence (SEQ ID NO:4) of the protein, as presented in FIG. 6 of Yamamoto et al., *Cell* 39:27–38 (1984), at page 31, which article is hereby entirely incorporated herein by reference.

FIG. 19 shows a comparison between the sequence of urinary soluble LDL receptor (SEQ ID NO:5) and the known sequence of the first 50 N-terminal residues of the precursor-LDL receptor (SEQ ID NO:2). Residues 1–21 of SEQ ID NO:2 of the precursor-LDL receptor are the signal peptide. Residues 22–24 of SEQ ID NO:2 are missing in mature soluble LDL receptor, e.g., as presented in FIG. 15.

DETAILED DESCRIPTION OF THE PREFERRED EMBODIMENTS

Figure 2:
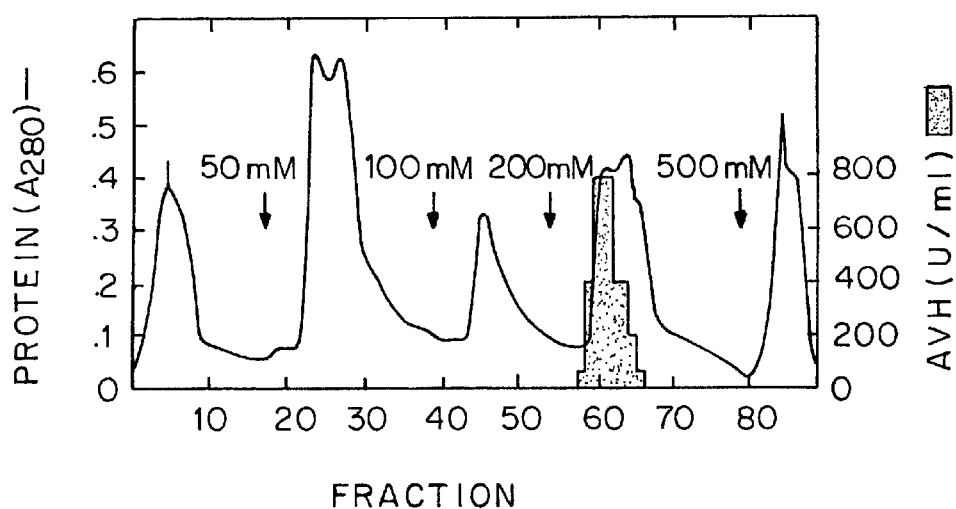
FIG. 2 shows the elution pattern of the proteins and antiviral activity from a TSK-DEAE anion exchange column.

It has been found that interferon-treated cells secrete into the culture medium an antivirally active protein which is not an interferon. This protein is not neutralized by antibodies directed against any of the three types of human interferons (both NIH standards and neutralizing monoclonal antibodies). The protein was identified as comprising the extracellular ligand binding domain of the LDL receptor.

The soluble LDL receptor is secreted into the culture medium by mammalian cells that enter into an antiviral state in response to any interferon. Examples are fibroblast cells or epithelial cells derived from amniotic fluid, e.g. U cells, WISH cells. It also can be found in the urine of healthy human individuals.

In contrast to interferons, the soluble LDL receptor does not induce in the cells an antiviral state, but is antiviral by itself. Thus, cells treated simultaneously with the soluble LDL receptor and virus will not lyse, while cells treated with virus alone or simultaneously with virus and IFN-γ, will be infected and lyse after 12 hours. This shows that IFN-γ gives no immediate protection to the cells against virus since it takes about 10 hours until the antiviral state is established in cells treated with IFN-γ. In contrast, the soluble LDL receptor protects the cells immediately when added to them.

When examined by size exclusion chromatography, the soluble LDL receptor has an apparent molecular weight of about 40,000.

For the production of the soluble LDL receptor, suitable cells grown in culture are treated with an IFN in a suitable medium and then incubated for some hours at 37° C., thus producing the soluble LDL receptor which is secreted into the medium and can be isolated from the supernatant. Suitable cells are those which enter into an antiviral state in response to an interferon. Similar results were obtained with IFN-α, IFN-β and IFN-γ, but IFN-γ is preferably used because it does not exhibit antiviral activity under the conditions of the antiviral assay for the soluble LDL receptor (simultaneous addition of the soluble LDL receptor and challenge virus to the cell culture).

In a preferred embodiment of the invention, human WISH cells are treated with IFN-γ in MEM supplemented with a serum substitute and then further incubated at 37° C. The highest titer of the soluble LDL receptor was obtained after 17 hours. The supernatant of the cells containing the soluble LDL receptor is then harvested and concentrated by known methods, such as by ultrafiltration or by dialysis against semi-solid polyethylene glycol 20,000. The concentrated supernatant is then purified by chromatographic procedures.

In a preferred embodiment, purified soluble LDL receptor may be produced by a process comprising the following steps:

(a) growing human WISH cells in culture to confluency, inducing the cells with 30 U/ml IFN-γ in a serum-free medium and, after about 17 hours, harvesting the culture supernatant;

(b) concentrating said supernatant about 30-fold by, e.g., ultrafiltration with a membrane of molecular weight cut-off of about 10,000;

(c) subjecting said concentrated supernatant of step (b) to anion exchange chromatography to obtain partially purified active fractions of the antiviral factor;

(d) applying said partially purified fraction from step (c) to chromatography on a hydroxyapatite column to obtain partially purified fractions of the antiviral factor;

(e) applying said partially purified fraction from step (d) to anion exchange HPLC to obtain partially purified fractions of the antiviral factor;

(f) applying said partially purified fractions from step (e) to hydrophobic interaction chromatography to obtain partially purified fractions of the antiviral factor; and (g) applying said partially purified active fractions from step (f) to reversed phase high pressure liquid chromatography (HPLC) at about neutral pH to obtain partially purified antiviral factor. This step is then repeated to obtain homogeneous antiviral factor, defined by its ability to inhibit the cytopathic effect (CPE) exerted by vesicular stomatitis virus (VSV) on human WISH cells.

The ion exchange chromatography of step (c) is preferably performed on a TSK-DEAE column (Tosoh Corp., Japan) at PH about 8 eluted with increasing salt concentration. The hydroxyapatite chromatography is preferably performed on a Biogel HTP column (BioRad, USA) at pH 6.8 with phosphate buffers as eluants. The anion exchange HPLC is preferably performed on a SUPERFORMANCE TMAE column in a manner similar to the TSK-DEAE step. The hydrophobic interaction chromatography is preferably performed on a phenyl sepharose column eluted with decreasing salt concentration. The reversed phase HPLC is preferably performed on an AQUAPORE RP300 column, at PH 7.5, with a gradient of acetonitrile.

In another preferred embodiment soluble LDL receptor is purified by a process comprising at least steps (a), (b) and (c) as described in the aforementioned embodiment and then performing a step of immunoaffinity chromatography on a column of a monoclonal antibody directed against the soluble LDL receptor.

The monoclonal antibody can preferably be the one made by hybridoma C7 (ATCC, CRL 1691). The partially purified soluble LDL receptor is loaded onto the columns at neutral pH, the column is washed with 0.5M NaCl at neutral pH and the soluble LDL receptor is eluted in an enhanced state of purity with 50 mM $Na_2CO_3$ (pH 11) and immediately neutralized.

Preferably, in all steps of the purification the chromatography is monitored by measuring the protein concentration (absorbance at 280 nm or relative fluorescence following "on-line" reaction of representative aliquots with flourescamine). The antiviral activity in each fraction is determined by inhibition of the VSV-induced CPE in WISH cells according to the bioassay described herein.

In another preferred embodiment, soluble LDL receptor can be purified from the urine of healthy, human individuals. It may also be found in other biological fluids, such as blood serum, lymph, cerebral spinal fluid, saliva, and fractions thereof. The method of isolating and/or purifying soluble LDL receptor from a biological fluid may include a process comprising at least one of the above steps (b)–(g), wherein at least one of steps (b)–(g) may be replaced by affinity chromatography using monoclonal antibodies specific for an epitope of a soluble LDL receptor protein.

Alternatively, isolation and/or purification of soluble LDL receptor from biological samples, such as urine, may comprise (1) concentrating the fluid sample by microfiltration and/or ultrafiltration; (2) affinity chromatography using monoclonal antibodies specific for soluble LDL receptor; (3) reverse phase HPLC; and/or optionally, (4) size exclusion chromatography; in order to isolate the soluble LDL receptor, which protein does not naturally occur isolated from other naturally occuring proteins. In the above method, step (4) is optional, since the fraction obtained after the reverse phase HPLC step maybe of sufficient purity.

In the above alternative isolation and purification method of soluble LDL receptor from a biological fluid sample, it is preferred that the biological fluid sample be subjected to microfiltration using a pore size of 0.45 micron or smaller, such as 0.4, 0.3, 0.25, 0.2, or 0.1 microns. Additionally, it is preferred that the biological sample be additionally or alternatively subjected to ultrafiltration using a molecular weight cutoff selected from the group consisting of 70 K, 60 K, 50K, 40 K, 30 K, 20 K, 10 K and/or 5 K.

In a preferred embodiment, monoclonal antibodies used in the affinity chromatography step (2) may be specific for a soluble portion of an LDL receptor, as presented herein. In a preferred embodiment, the monoclonal antibody is cross reactive with a monoclonal antibody produced by hybridoma C7 (ATCC, CRL 1691).

In the affinity chromatography step (3) it is preferred that the partially purified soluble LDL receptor be loaded onto the column(s) at neutral pH, the column be washed with 0.5 M NaCl at neutral pH, and the soluble LDL receptor eluted in an enhanced state of purity with 50 mM $Na_2CO_3$ (pH 11) and immediately neutralized, such as with an acid, such as with 3M acetic acid.

It is also preferred that the resulting fractions in the above step be tested for antiviral activity, as presented herein wherein the fractions containing the highest activities are used for the next purification and/or isolation step. The antiviral activity may be determined, for example, by showing inhibition of cytopathic effect (CPE) asserted by vesicular stomatitis virus (VSV) on human WISH cells.

In another preferred embodiment, in the RP-HPLC step (3), the column(s) are preferably preequilibrated with 20 mM Hepes buffer at pH 7.5 and the column is then washed and the protein eluted by using an acetonitrile gradient in the same buffer. In one preferred embodiment, the antiviral activity is eluted or in the range of 10–20% acetonitrile, such as 12–18, 13–15, and 14–16% acetonitrile, wherein 14% is preferred. Antiviral active fractions may then preferably be tested and collected for further purification or sequencing.

In another preferred embodiment, optional step (4) as size exclusion chromatography, the soluble LDL receptor-containing fraction from a biological fluid is mixed with larger proteins, such as at least one selected from the group consisting of bovine serum albumen (BSA), human immunoglobulin, and carbonic anhydrate in phosphate buffered saline (PBS). The resulting mixture is used as the sample to be applied to the size exclusion chromatography column under near physiological conditions. The human immunoglobulin, BSA and carbonic anhydrate are used as molecular weight markers. Preferably the antiviral activity eluted peak has an apparent molecular weight of 25–35 Kda, such as 26–34, 26–33, 26–32, 27–31, or about 27–30 KDa molecular weight, as determined according to size exclusion chromatography or SDS PAGE, (under reducing or nonreducing conditions).

Preferably in all steps of the purification, the LDL receptor protein containing fractions are monitored by measuring the protein-concentration, e.g., absorbance at 280 nm or relative fluorescence following "on-line" reaction of representative aliquots with flourescamine. The antiviral activity in each fraction is also determined by inhibition of VSV induced CPE WISH cells, according to known method steps, e.g., as described herein.

LDL receptor protein-containing fractions from the RP-HPLC step, or further following size exclusion chromatography step, can be used according to known method steps, to provide purified LDL receptor protein in sequencable form, which can then be sequenced, according to the present invention. In a preferred embodiment, the LDL receptor fractions are absorbed on a PVDF membrane and subjected to microsequence analysis on a protein microsequencer, as commercially available, and/or is known to those skilled in the art.

As used herein the term "muteins" refers to analogues of the soluble LDL receptor in which one or more of the amino acid residues of the natural soluble LDL receptor, preferably 1–10 and more preferably 1–5 residues or even only a single residue, are replaced by different amino acid residues or are deleted, or one or more amino acid residues, such as 1–10, 1–5 or only one residue are added to the natural sequence of the soluble LDL receptor, without changing considerably the antiviral activity of the resulting product. These muteins are prepared by known synthesis and/or site-directed mutagenesis techniques, or any other known technique suitable therefor. The substitutions are preferably conservative. See, e.g., Schulz, G. E. et al., *Principles of Protein Structure*, Springer-Verlag, New York, 1978, and Creighton, T. E., *Proteins: Structure and Molecular Properties*, W. H. Freeman & Co., San Francisco, 1983, which are hereby incorporated by reference.

The types of such substitutions which may be made in the protein or peptide molecule of the present invention may be based on analysis of the frequencies of amino acid changes between a homologous protein of different species, such as those presented in Table 1–2 of Schulz et al. (supra) and FIGS. 3–9 of Creighton (supra). Based on such an analysis, conservative substitutions may be defined herein as exchanges within one of the following five groups:

1. Small aliphatic, nonpolar or slightly polar residues: ala, ser, thr (pro, gly);
2. Polar, negatively charged residues and their amides: asp, asn, glu, gln;
3. Polar, positively charged residues: his, arg, lys;
4. Large aliphatic, nonpolar residues: met, leu, ile, val (cys); and
5. Large aromatic residues: phe, tyr, trp.

The three amino acid residues in parentheses above have special roles in protein architecture. Gly is the only residue lacking any side chain and thus imparts flexibility to the chain. Pro, because of its unusual geometry, tightly constrains the chain. Cys can participate in disulfide bond formation which is important in protein folding. Note that Schulz et al. would merge Groups 1 and 2, above. Note also that Tyr, because of its hydrogen bonding potential, has some kinship with Ser, Thr, etc.

Conservative amino acid substitutions according to the present invention, e.g., as presented above, are known in the art and would be expected to maintain biological and structural properties of the polypeptide after amino acid substitution. Most deletions and insertions, and substitutions according to the present invention are those which do not produce radical changes in the characteristics of the protein or peptide molecule. One skilled in the art will appreciate that the effect of substitutions can be evaluated by routine screening assays, either immunoassays or bioassays. For example, a mutant typically is made by site-specific mutagenesis of the peptide molecule-encoding nucleic acid, expression of the mutant nucleic acid in recombinant cell culture, and, optionally, purification from the cell culture, or a biological sample containing a soluble LDL receptor protein, for example, by immunoaffinity chromatography using a specific antibody on a column (to absorb the mutant by binding to at least one epitope).

The term "fused protein" refers to a polypeptide comprising the soluble LDL receptor or a mutein thereof fused with another protein which has an extended residence time in body fluids. The soluble LDL receptor may thus be fused to another protein, polypeptide or the like, e.g., an immunoglobulin or a fragment thereof.

The term "salts" herein refers to both salts of carboxyl groups and to acid addition salts of amino groups of the soluble LDL receptor, muteins and fused proteins thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid.

"Functional derivatives" as used herein cover derivatives of the soluble LDL receptor and its fused proteins and muteins, which may be prepared from the functional groups which occur as side chains on the residues or the N- or C-terminal groups, by means known in the art, and are included in the invention as long as they remain pharmaceutically acceptable, i.e. they do not destroy the activity of the protein and do not confer toxic properties on compositions containing it. These derivatives may, for example, include polyethylene glycol side-chains which may mask antigenic sites and extend the residence of the soluble LDL receptor in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or acyl derivatives of free hydroxyl groups (for example that of seryl or threonyl residues) formed with acyl moieties. The term "functional derivative" also includes proteins which have an amino acid sequence longer or shorter than the sequence determined, as long as the protein still has the ability to inhibit viral infection.

As "active fractions" of the soluble LDL receptor, its fused proteins and its muteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has the ability to inhibit viral infection and/or activity. Such active fractions can be readily determined by testing smaller and smaller portions of the entire soluble LDL receptor or mutein to find the smallest fragment which retains the ability to inhibit viral infections. Any fractions containing the smallest active fraction will also be an active fraction. Undue experimentation would not be involved as the required tests for antiviral activity (as described herein) may be routinely carried out.

This invention further concerns DNA molecules comprising the nucleotide sequence encoding the soluble LDL receptor, fused proteins, muteins or active fractions thereof, replicable expression vehicles containing said DNA molecules, hosts transformed therewith and protein produced by expression of such transformed hosts. The term "DNA molecules" includes genomic DNA, cDNA, synthetic DNA and combinations thereof.

The production of the recombinant soluble LDL receptor may be carried out by different techniques. According to one approach, the known cDNA of the entire human LDL receptor is taken from plasmid pLDLR-2 (Yamamoto et al., op cit.). The DNA is subjected to site directed mutagenesis with appropriate oligonucleotides so that a termination codon and a polyadenylation site are inserted after codon 292 of the mature LDL receptor. This construct is then inserted into appropriately constructed expression vectors by techniques well known in the art (see Maniatis et al., op cit.). Double-stranded cDNA is linked to plasmid vector by homopolymeric tailing or by restriction linking involving the use of synthetic DNA linkers or blunt-ended ligation techniques. DNA ligases are used to ligate the DNA molecules and undesirable joining is avoided by treatment with alkaline phosphatase.

The production of a fused protein comprising the ligand binding domain of the LDL receptor and, e.g., the constant region of IgG2 heavy chain may be carried out as follows: the DNA of PLDLR is subjected to site-directed mutagenesis with appropriate oligonucleotides so that a unique restriction site is introduced immediately after codon 292 of the mature LDL receptor. A plasmid bearing the constant region of IgG2 heavy chain, e.g., pRKCO4$_2$Fc$_1$ (Byrn R. A. et al., 1990 Nature (London) 344, 667–670) is subjected to similar site-directed mutagenesis to introduce the same unique restriction site as close as possible to Asp 216 of IgG$_1$ heavy chain in a way that allows translation in phase of the fused protein. A dsDNA fragment consisting of 5' untranslated sequences and encoding the leader and about the first 295 amino acids of LDL receptor is prepared by digestion of the mutated pLDL receptor at the EcoRI and the unique restriction sites. The mutated pRKCD4$_2$Fc$_1$ is similarly digested to generate a large fragment containing the plasmid and the IgG$_1$ sequences. The two fragments are then ligated to generate a new plasmid encoding a polypeptide consisting of about the N-terminal 295 acids of LDL receptor and about 227 C-terminal amino acids of IgG$_1$ heavy chain (hinge region and CH2 and CH3 domains). The DNA encoding the fused protein may be isolated from the plasmid by digestion with EcoRI and then inserted into an efficient expression vector.

In order to be capable of expressing the soluble LDL receptor, its muteins or the fused proteins, an expression vector should comprise also specific nucleotide sequences containing transcriptional and translational regulator information linked to the DNA coding for the desired protein in such a way as to permit gene expression and production of the protein. First, in order for the gene to be transcribed, it must be preceded by a promoter recognizable by RNA polymerase, to which the polymerase binds and thus initiates the transcription process. There are a variety of such promoters in use, which work with different efficiencies (strong and weak promoters). They are different for prokaryotic and eukaryotic cells.

The promoters that can be used in the present invention may be either constitutive, for example, the int promoter of bacteriophage lambda$_1$ the bla promoter of the β-lactamase gene of pBR322, and the CAT promoter of the chloramphenicol acetyl transferase gene of pPR325, etc., or inducible, such as the prokaryotic promoters including the major right and left promoters of bacteriophage lambda (P$_1$ and P$_r$), the trp, recA, lacZ, lacI, ompF and gal promoters of E. coli, or the trp-lac hybrid promoter, etc. (Glick, B. R. (1987) J. Ind. Microbiol. 1:277–282).

Besides the use of strong promoters to generate large quantities of mRNA, in order to achieve high levels of gene expression in prokaryotic cells, it is necessary to use also ribosome-binding sites to ensure that the mRNA is efficiently translated. One example is the Shine-Dalgarno sequence (SD sequence) appropriately positioned from the initiation codon and complementary to the 3'- terminal sequence of 16 S RNA.

For eukaryotic hosts, different transcriptional and translational regulator sequences may be employed, depending on the nature of the host. They may be derived from viral sources, such as adenovirus, bovine papilloma virus, Simian virus, or the like, where the regulatory signals are associated with a particular gene which has a high level of expression. Examples are the TK promoter of Herpes virus, the SV40 early promoter, the yeast ga14 gene promoter, etc. Transcriptional initiation regulatory signals may be selected which allow for repression and activation, so that expression of the genes can be modulated.

The DNA molecule comprising the nucleotide sequence coding for the soluble LDL receptor of the invention or its fragments or muteins or fused proteins thereof, and the operably linked transcriptional and translational regulator signals is inserted into a vector which is capable of integrating the desired gene sequences into the host cell chromosome. In order to be able to select the cells which have stably integrated the introduced DNA into their chromosomes, one or more markers which allow for selection of host cells which contain the expression vector is used. The marker may provide for prototropy to an auxotrophic host, biocide resistance, e.g., antibiotics, or heavy metals, such as copper, or the like. The selectable marker gene can either be directly linked to the DNA gene sequences to be expressed, or introduced into the same cell by cotransfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, H., (1983) Mol. Cel. Biol. 3:280.

In a preferred embodiment, the introduced DNA molecule will be incorporated into a plasmid or viral vector capable of autonomous replication in the recipient host. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in E. coli, for example, pBR322, ColE1, pSC101, pACYC 184, etc. (see Maniatis et al., op. cit.); Bacillus plasmids such as pC194, pC221, pT127, etc. (Gryczan, T., "The Molecular Biology of the Bacilli", Academic Press, N.Y. (1982), pp. 307–329); Streptomyces plasmids including pIJ101 (Kendall, K. J. et al., (1987) J. Bacterial. 169:4177–4183); Streptomyces bacteriophages such as φC31 (Chater, KF. et al., in "Sixth International Symposium on Actinomycetales Biology", Akademiai Kaido, Budapest, Hungary (1986), pp. 45–4), and Pseudomonas plasmids (John, J. F., et al. (1986) Rev. Infect. Dis. 8:693–704), and Izaki, K. (1978) Jpn. J. Bacterial. 33:729–742).

Preferred eukaryotic plasmids include BPV, vaccinia, SV40, 2-micron circle, etc., or their derivatives. Such plasmids are well known in the art (Botstein, D., et al. (1982) Miami Wint. Symp. 19:265–274; Broach, J R., in "The Molecular Biology of the Yeast Saccharomyces: Life Cycle and Inheritance", Cold Spring Harbor Laboratory, Cold Spring Harbor, N.Y., pp. 445–470 (1981); Broach, J. R., (1982) Cell 28:203–204; Bollon, D. P., et al. (1980) J. Clin. Hematol. Oncol. 10:39–48; Maniatis, T., in "Cell Biology: A Comprehensive Treatise, Vol. 3: Gene Expression," Academic Press, N.Y., pp. 563–608 (1980)).

Once the vector or DNA sequence containing the construct(s) has been prepared for expression, the expression vector may be introduced into an appropriate host cell by any variety of suitable means, such as transformation, transfection, lipofection, conjugation, protoplast fusion, electroporation, calcium phosphate precipitation, direct microinjection, etc.

Host cells to be used in this invention may be either prokaryotic or eukaryotic. Preferred prokaryotic hosts include bacteria such as *E. coli*, Bacillus, Streptomyces, Pseudomonas, Salmonella, Serratia, etc. The most preferred prokaryotic host is *E. coli*. Bacterial hosts of particular interest include *E coli* K12 strain 294 (ATCC 31446), *E. coli* X1776 (ATCC 31537), *E. coli* W3110 (F-, lambda-, prototrophic (ATCC 27325)), and other enterobacterium such as *Salmonella typhimurium* or *Serratia marcescens* and various Pseudomes species. Under such conditions, the protein will not be glycosylated. The prokaryotic host must be compatible with the replicon and control sequences in the expression plasmid.

However, since the soluble LDL receptor is a cysteine rich protein, eukaryotic hosts are preferred over prokaryotic hosts. Preferred eukaryotic hosts are mammalian cells, e.g., human, monkey, mouse and chinese hamster ovary (CHO) cells, because they provide post-translational modifications to protein molecules including correct folding, correct disulfide bond formation as well as glycosylation at correct sites. Also yeast cells and insect cells can carry out post-translational peptide modifications including high mannose glycosylation. A number of recombinant DNA strategies exist which utilize strong promoter sequences and high copy number of plasmids which can be utilized for production of the desired proteins in yeast and in insect cells. Yeast cells recognize leader sequences on cloned mammalian gene products and secrete peptides bearing leader sequences.

After the introduction of the vector, the host cells are grown in a selective medium, which selects for the growth of vector-containing cells. Expression of the cloned gene sequence(s) results in the production of the soluble LDL receptor, a fusion protein, or a mutein or a fragment thereof. The expressed protein is then isolated and purified by any conventional procedure involving extraction, precipitation, chromatography, electrophoresis, or the like, or by affinity chromatography, using anti-soluble LDL receptor monoclonal antibodies (e.g., hybridoma C7, Belsiegel U. et al., J. Biol. Chem., 256:11923–11931, 1981) immobilized on a gel matrix contained within a column. Crude preparations containing said recombinant soluble LDL receptor are passed through the column whereby the soluble LDL receptor will be bound to the column by the specific antibody while the impurities will pass through. After washing, the protein is eluted from the gel at a high pH, e.g., pH 11.

The soluble LDL receptor and its muteins, fused proteins and their salts, functional derivatives, and active fractions thereof are indicated for the treatment of viral diseases in mammals.

The present invention further relates to pharmaceutical compositions comprising a pharmaceutically acceptable carrier and the soluble LDL receptor of the invention or its active muteins, fused proteins and their salts, functional derivatives or active fractions thereof, either as the sole active ingredient or in combination with other antiviral agents, e.g., interferons. These compositions may be used against viral diseases. The way of administration can be via any of the accepted modes of administration for similar agents and will depend on the condition to be treated, e.g., intravenously or intramuscularly or subcutaneously, in case of systemic viremia, or local injection or topical application in case of a localized infection, or continuously by infusion, etc.

The pharmaceutical compositions of the invention are prepared for administration by mixing the soluble LDL receptor its derivatives, alone or together with other antiviral agents, with physiologically acceptable carriers, stabilizers and excipients, and prepared in dosage form, e.g., by lyophilization in dosage vials. The amount of active compound to be administered will depend on the route of administration, the disease to be treated and the condition of the patient. Local injection, for instance, will require a lower amount of the protein on a body weight basis than will intravenous infusion in case of systemic viremia.

Effective amounts of a soluble LDL receptor protein or composition, are from about 0.01 $\mu$g to about 100 mg/kg body weight, and preferably from about 10 $\mu$g to about 50 mg/kg body weight, such as 0.05, 0.07, 0.09, 0.1, 0.5, 0.7, 0.9, 1, 2, 5, 10, 20, 25, 30, 40, 45, 50, 55, 60, 65, 70, 75, 80, 85, 90, 95 or 100 mg/kg. See, e.g., Berkow et al, eds., The Merck Manual, 16th edition, Merck and Co., Rahway, N.J., 1992; Goodman et al., eds., Goodman and Gilman's The Pharmacological Basis of Therapeutics, 8th edition, Pergamon Press, Inc., Elmsford, N.Y., (1990); *Avezy's Drug Treatment: Principles and Practice of Clinical Pharmacology and Therapeutics,* 3rd edition, ADIS Press, LTD., Williams and Wilkins, Baltimore, Md. (1987), Ebadi, *Pharmacology*, Little, Brown and Col, Boston, (1985), Katzung, *Basic and Clinical Phamacology*, Appleton and Lange, Norwalk, Conn., (1992), which references and references cited therein, are entirely incorporated herein by reference.

The invention will now be illustrated by the following non-limiting examples.

EXAMPLES

Example 1

Preliminary Identification of the Antiviral Activity of the Soluble LDL Receptor The presence of an unknown antiviral factor in the supernatant of IFN-induced cells was shown by several experiments.

The antiviral effect was determined by the virus cytopathic effect (CPE) reduction assay (Rubinstein, S. et al (1981) J. Virol. 37:755–758) using human WISH cells and VSV as a challenge. Initial studies were performed with IFN-$\alpha$, IFN-$\beta$ and IFN-$\gamma$ and similar results were obtained with all three IFNs.

In the experiment described in FIG. 1, and summarized in Table 1, human amino WISH cells (ATCC CCL-25) were seeded in a 96-well microtiter plate. A few hours later, serial twofold dilutions (from right to left), starting with 50 U/ml of IFN-$\alpha$, IFN-$\beta$ and IFN-$\gamma$ in MEM (Minimal Essential Medium) supplemented with 10% fetal bovine serum, were applied to monolayers of the cells in rows (from top) 1–3, 4–6 and 7–9, respectively, and the cells were incubated overnight at 37° C. The medium in rows 1, 5 and 9 was not removed. The medium in rows 2, 6 and 10 was aspirated, the cell monolayers were washed once and fresh medium was added. In rows 3, 7 and 11, the medium was replaced with fresh dilutions of the respective IFNs, and in rows 4, 8 and 12, neutralizing antibodies specific to IFN-$\alpha$, IFN-$\beta$ (NIH standards) and to IFN-$\gamma$ (monoclonal antibody 166.5, described in Novick et al., (1983) EMBO 3(2), p. 1527) were added respectively. VSV in growth medium was applied to the cells in all wells. The infected cultures were further incubated overnight and then stained with crystal violet, in order to better evaluate visually the extent of the virus cytopathic effect.

TABLE 1

The role of antiviral factor in IFN action

| Row of FIG. 1 | Treatment[1] | 50% CPE dilution | units/ml[2] | % of activity |
|---|---|---|---|---|
| 1 | IFN-α 24 hrs, standard assay | 400 | 1000 | 100 |
| 2 | IFN-α 24 hrs, wash | 100 | 250 | 25 |
| 3 | IFN-α 24 hrs, replace IFN | 200 | 250 | 25 |
| 4 | IFN-α 24 hrs, neutralize | 300 | 375 | 37 |
| 5 | IFN-β 24 hrs, standard assay | 400 | 1000 | 100 |
| 6 | IFN-β 24 hrs, wash | 200 | 500 | 50 |
| 7 | IFN-β 24 hrs, replace IFN | 400 | 1000 | 100 |
| 8 | IFN-β 24 hrs, neutralize | 400 | 1000 | 100 |
| 9 | IFN-γ 24 hrs, standard assay | 800 | 1000 | 100 |
| 10 | IFN-γ 24 hrs, wash | 200 | 250 | 25 |
| 11 | IFN-γ 24 hrs, replace IFN | 400 | 500 | 50 |
| 12 | IFN-γ 24 hrs, neutralize | 800 | 1000 | 100 |

[1]In the standard assay, (rows 1, 5 and 9) IFN was added in serial twofold dilutions (from right to left in FIG. 1) to monolayers of WISH cells in 96-well plates. After 24 hrs, VSV was added and 18 hrs later the cells were fixed and stained. In other cases, washing (rows 2, 6 and 10), replacement with IFN in fresh medium (rows 3, 7 and 11) or addition of anti-IFN neutralizing antibodies (rows 4, 8 and 12), were done immediately prior to challenge with VSV.

The titers of IFN standards (rows 1, 5 and 9) were designated as 1000 U/ml.

The dilutions at which NIH standard IFNs (rows 1, 5 and 9) gave 50% CPE were first determined. As seen in FIG. 1, rows 2, 6 and 10, washing off the cells after 24 hrs and prior to VSV challenge, significantly reduced the potency of all three IFNs. Replacement of the medium with fresh dilutions of IFN reduced the level of protection with IFN-α (row 3) and IFN-γ (row 1), but not with IFN-β (row 7). Addition of neutralizing anti-IFN antibodies to the growth medium after 24 hrs exposure to IFN, had only a small effect on the activity of IFN-α (row 4) and no effect on the activity of IFN-β and IFN-γ (rows 8 and 12, respectively).

Since IFNs induce antiviral state in cells after interaction with specific cell surface receptors, they can be removed once the antiviral state is established and the cells will remain protected against the virus. Therefore, removal of IFN after the antiviral state was established, is not expected to affect the apparent IFN potency. However, in the above experiment, it was shown that the apparent antiviral potency of a given IFN sample was significantly lower if the culture medium was replaced prior to challenge with virus (rows 2, 6 and 10). Even if the medium was replaced with fresh IFN, both in the case of IFN-α (row 3) and IFN-γ (row 11) the level of protection was lower than without replacement. Hence the culture medium had a non interferon component that protects the cells from virus infection.

Incubation of the cells after application of IFN and addition of anti-IFN neutralizing antibodies prior to virus challenge without replacement of the growth medium, lowered the antiviral activity of the IFN-α only slightly (row 4) and not the activity of IFN-β or IFN-γ (rows 8 and 12, respectively). These results suggest that the reduced activity observed when the IFN-containing medium was removed, is not due to removal of the IFN molecules, but rather to removal of other molecules which are required to achieve full antiviral protection.

The antiviral enhancing activity in the medium, was herein demonstrated in vitro in the IFN CPE reduction assay. It is possible that the active extracellular component, plays also a role in vivo in the IFN antiviral activity. When IFN is used in a systemic disease where secreted components are eliminated continuously, administration of such a factor might greatly enhance the effect of IFN.

Example 2

Production and Purification of the Antiviral Protein 2.1 Production of Crude Antiviral Protein Human amino cells WISH (ATCC CCL-25) were grown to confluency on FIBRACELL discs (Sterilin, U.K.) in spinner flasks, in a medium consisting of MEM supplemented with 10% fetal calf serum (FCS). At confluency, the medium was discarded and the discs washed several times with serum-free MEM. The cells were then incubated in MEM (1.3 l) supplemented with a protein-free serum substitute ADC-1 (1:50, Biological Industries, Beit Haemek, Israel), Hepes 20 mM, Insulin 0.2 μg/ml and IFN-γ (30 U/ml). Incubation was continued for 17 hrs at 37° C. The culture medium was then collected, spun (5000 xg, 15 min) and the supernatant was collected and kept under sterile conditions at 4° C. for short periods (up to 24 hrs), or at −20° C. until used. The cell culture could be continuously used for production by adding more protein-free medium and IFN-γ.

2.2 Concentration of Crude Antiviral Factor

The antiviral factor can be concentrated either by dialysis against polyethylene glycol 20,000 or by ultrafiltration. Crude cell supernatant (1.5 l) of step 2.1 above was concentrated about 30-fold by ultrafiltration in a MINITAN unit (Millipore, USA) with a polysulfone membrane of molecular weight 10,000 cut off (PTGC MINITAN plate). The crude retentate was washed with sodium borate buffer, 20 mM, pH 8 (Buffer A) and brought to a volume of about 50 ml. This material was used immediately or kept frozen at −20° C. until used.

2.3 Chromatography on TSK-DEAE

A TSK-DEAE column (2.5×33 cm, Tosoh, Japan) was equilibrated with Buffer A. Concentrated antiviral factor from MINITAN step 2.2 above was applied to the column at a flow rate of 8 ml/min. The column was then washed with Buffer A and eluted stepwise with 50, 100, 200 and 500 mM NaCl in Buffer A. Fractions of 12 ml were collected and subjected to bioassay. The column was monitored by absorbance at 280 nm (FIG. 2). The protein peak eluted with 200 mM NaCl, contained antiviral activity when tested in the presence of neutralizing anti IFN-γ monoclonal antibody No. 166-5. It was pooled and concentrated to a volume of about 20 ml by ultrafiltration on a YM-10 membrane (MW cut off 10,000, Amicon USA). The material was kept at −20° until used.

2.4 Hydroxyapatite Chromatography

Figure 3:
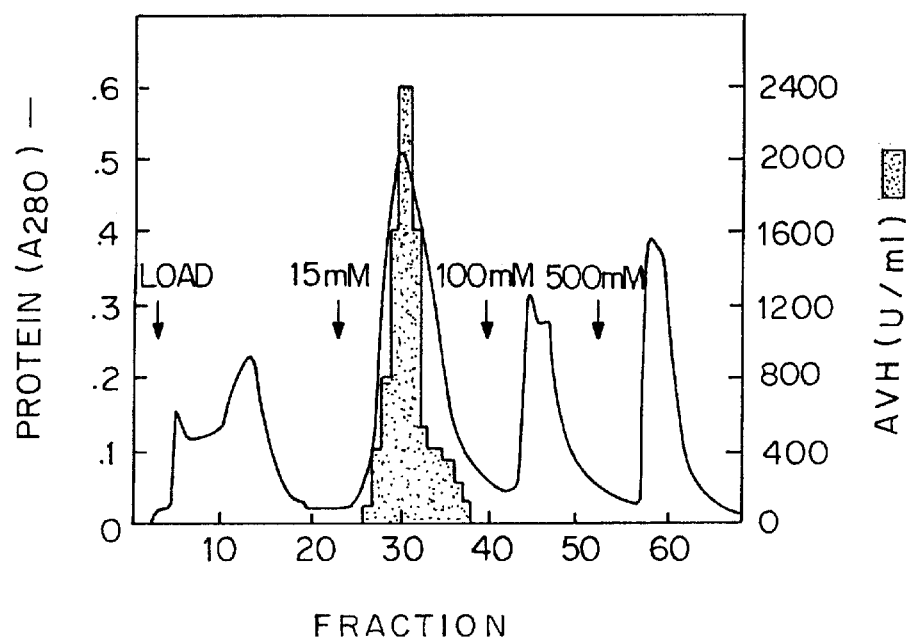
FIG. 3 shows the elution pattern of proteins and antiviral activity from a hydroxyapatite Biogel HTP column.

A hydroxyapatite biogel HTP column (2.5×4 cm, BioRod, USA) was equilibrated with water. The concentrated 0.2 m NaCl protein peak of step 2.3 (166 mg) was loaded on the Biogel HTP column at a flow rate of 2 ml/min. The column was washed with water and eluted with 15 mM sodium phosphate pH 6.8. Fractions of 2 ml were collected and tested for antiviral activity. The column was monitored by absorbance at 280 nm (FIG. 3). The antiviral activity was found in the 15 mM phosphate eluate, pooled and concentrated by ultrafiltration.

2.5 Anion Exchange HPLC

Figure 4:
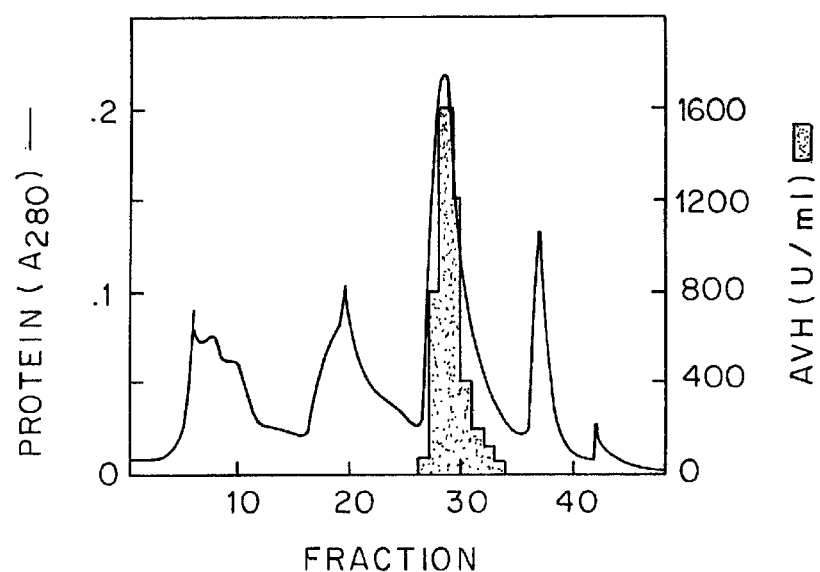
FIG. 4 shows the elution pattern of the proteins and antiviral activity from a SUPERFORMANCE TMAE-65-S anion exchange HPLC column.

An anion exchange HPLC column (SUPERFORMANCE-TMAE-650S, E. Merck, Germany) was pre-equilibrated with Buffer A. The concentrated pool containing 73 mg protein from step 2.4 was spun (10,000 xg, 5 min.) and the supernatant was applied to the column at a flow rate of 1 ml/min. The column was washed with Buffer A and then eluted stepwise by 50, 100, 200 and 500 mM NaCl in Buffer A. Fractions of 2.5 ml were collected and assayed for antiviral activity. The column was monitored at 280 nm (FIG. 4). The activity eluted in the 200 mM NaCl fraction. This fraction was pooled and kept at −20° C. until used.

2.6 Hydropohobic Interaction Chromatography

Figure 5:
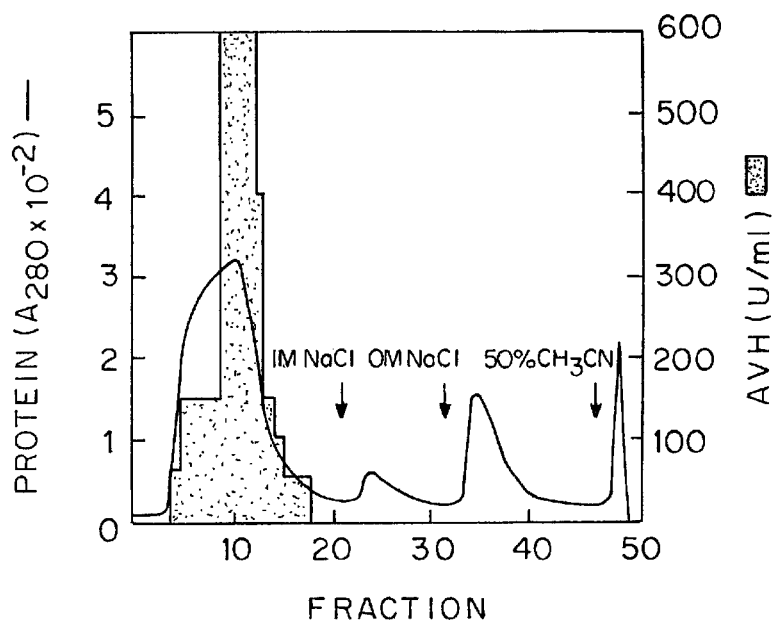
FIG. 5 shows the elution pattern of proteins and antiviral activity from a phenyl sepharose hydrophobic interaction column.

A phenyl sepharose column (1.5×6.5 cm, Pharmacia, Sweden) was equilibrated with 1.5 M NaCl in Buffer A. The 200 mM Na phosphate protein peak of step 2.5 (10 mg) was brought to 1.5 M NaCl and loaded (1 ml/min.) on the phenyl sepharose column. The column was washed with 1.5M NaCl in Buffer A and unbound protein peak was collected. The column was eluted stepwise with 1M NaCl in Buffer A, Buffer A and 50% $CH_3CN$/50% Buffer A. Antiviral activity was obtained in the unbound (1.5 M NaCl) fraction. The column was monitored at 280 nM (FIG. 5).

2.7 Reversed Phase HPLC

Figure 6:
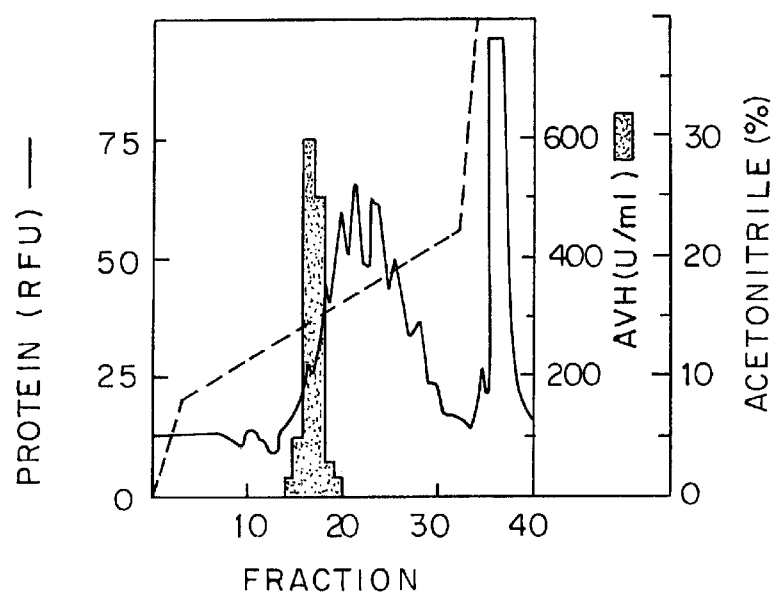
FIG. 6 shows the elution pattern of protein and antiviral activity from a reversed-phase AQUAPORE RP-300 HPLC column.

The unbound pooled fraction from step 2.6 (1.2 mg) was loaded on an AQUAPORE RP-300 RP-HPLC column (4.6× 30 mm) that was preequilibrated with 20 mM Hepes buffer pH 7.5. The column was washed and eluted at a flow rate of 0.5 ml/min by an acetonitrile gradient in the same buffer. Fractions of 1 ml were collected and tested for antiviral activity. The antiviral activity eluted at 14% acetonitrile and was associated with a protein peak. However, this peak was not completely resolved from adjacent peaks (FIG. 6). The column was monitored by a flourescamine-based post-column reaction system (Stein S. and Moschera J., 1981, Methods in Enzymology, 79:7–16).

Figure 7:
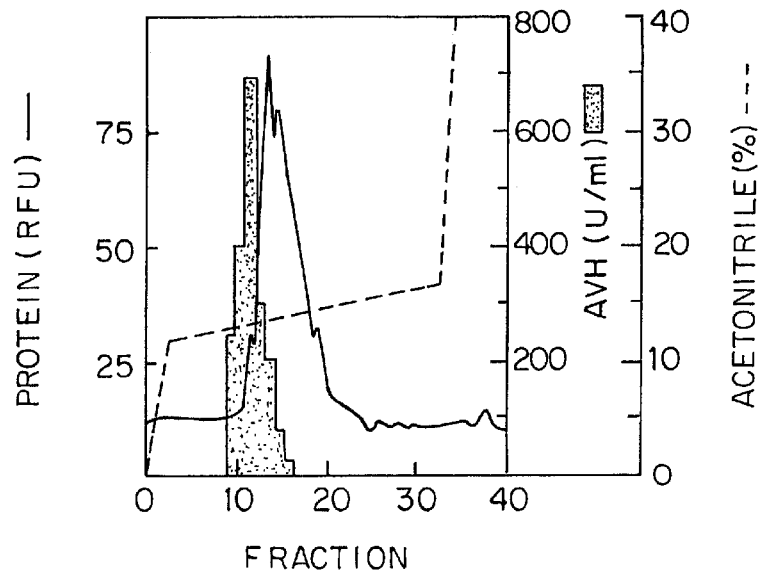
FIG. 7 shows the elution pattern of protein and antiviral activity from rechromatography on a reversed-phase HPLC column.
Figure 8:
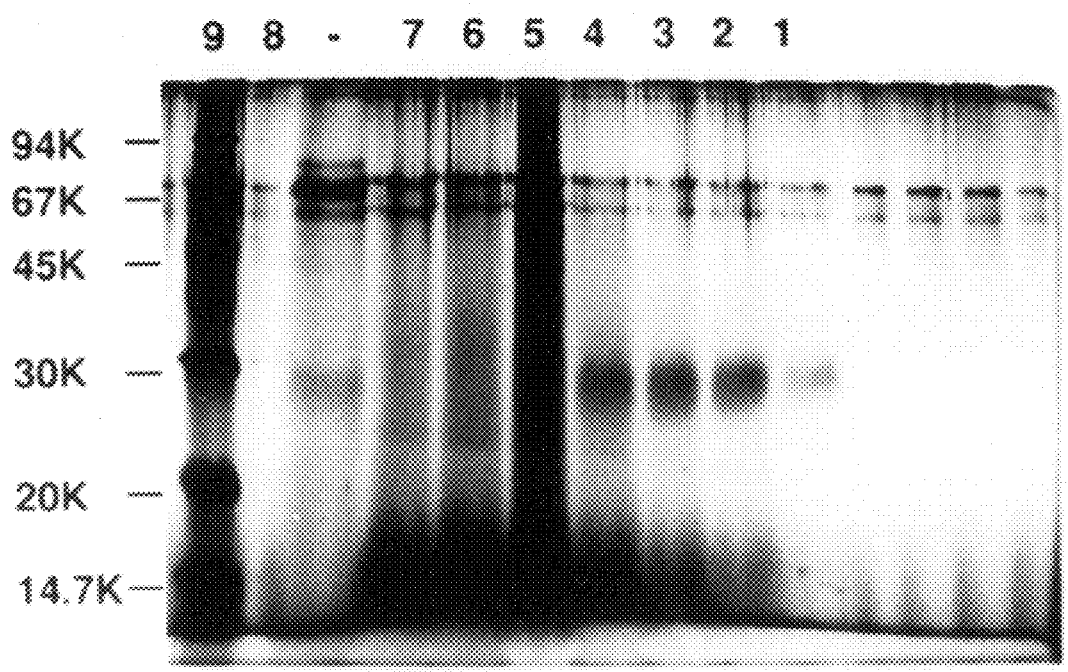
FIG. 8 shows sodium dodecyl sulfate-polyacrylamide gel electrophoretic (SDS-PAGE) analysis of various fractions obtained in the last step of the purification procedure. A 13% acrylamide gel was used and stained with silver. The lanes are: 1–7, aliquots (400 ul) of fractions 10–16 respectively from RP-300 chromatography (FIG. 7) which were concentrated by ultrafiltration; 8, control sample buffer; 9, molecular weight markers, indicated on the left side.

Active fractions (56 $\mu$g) were pooled, diluted twofold with 20 mM Hepes, pH 7.5 and rechromatographed on the AQUAPORE RP-300 column (FIG. 7). Aliquots (400 $\mu$l) of each fraction were concentrated by ultrafiltrition and subjected to polyacrylamide (13%) gel electrophoresis in the presence of sodium dodecyl sulfate and β-mercaptoethanol (SDS-PAGE). The protein bands were visualized by silver staining. The lanes are: lane 1–7, fractions 10–16 respectively of the HPLC; lane 8, control sample buffer; lane 9, molecular weight markers, indicated on the left side (FIG. 8).

Example 3

Characterization of the Antiviral Factor 3.1 Bioassay of Antiviral Activity

The assay is similar to the cytopathic effect (CPE) inhibition assay which is used for measuring IFN activity (Rubinstein S. et al., (1981) J. Virol. 37: 755–758). The antiviral activity is calibrated against NIH reference standard of human IFN-β. It can also be calibrated with IFN-α standard, but not with IFN-γ, which does not protect the cells from virus under these assay conditions. The following procedure is used:

Confluent monolayers of WISH cells are prepared on day 1, seeding 45,000 cells/well in 100 $\mu$l of MEM supplemented with 10% FCS, in 96-flat bottom well plates. The plates are incubated at 37° C. in 5% $CO_2$. On day 2, samples of the antiviral factor are diluted twofold serially in a separate plate (100 $\mu$l). Neutralizing monoclonal anti-IFN-γ antibody (166-5) sufficient for neutralizing 1000 U/ml of IFN-γ is added to each well and the solutions are transferred to the plate with the WISH cells, followed immediately by challenge with an appropriate amount (see below) of stock VSV (50 $\mu$l). The plates are incubated overnight at −37° C. The assay is calibrated against standard IFN-β. On day 3, about 20 hours following virus challenge, the cytopathic effect in control wells is observed microscopically. When it is ≧80%, the plates are drained and the monolayer is stained with crystal violet (0.5% in 70% Aq. methanol), washed with plenty of tap water and the end points are determined by observation under the microscope. An appropriate amount of VSV for this assay is the dilution of stock VSV which, when added to a serial twofold dilution of standard IFN-β under the assay conditions, will give 50% CPE at IFN-β dilution of about 3–6 U/ml after 20–24 hrs of incubation.

3.2 The Antiviral Factor is a Protein

Three experiments were performed in order to demonstrate that the antiviral factor is a protein.

a. Molecular weight >10,000, as shown by the ability to concentrate the antiviral activity by dialysis against PEG 20,000 and by ultrafiltration on membranes with cut-off of 10,000 Da, indicating that the antiviral factor is a macromolecule.

b. Heat lability. Active fraction from a MONO Q anion exchange step (same as step 2.5 of example 2) was heated in a 100° C. bath for 10 min and then tested for antiviral activity. No activity remained following this treatment. See Table 2.

c. Trypsin sensitivity. Active fraction from the MONO Q anion exchange step was incubated with TPCK-treated trypsin (Worthington) at 5:1 protein:enzyme ratio, respectively, overnight at room temperature. Control fraction was similarly kept without trypsin and control trypsin was made as well. It was found that 66% of the antiviral activity was lost by trypsin treatment and hence, it was concluded that the antiviral factor is trypsin sensitive. See Table 2.

d. The antiviral factor is not an interferon. Interferon is defined as a protein which induces in cells an antiviral state which persists even after removal of the interferon. Cells were incubated with antiviral factor-containing medium from the MONO Q step for 24 hrs, the medium was removed, the cells were washed and challenged with VSV. No protection from VSV was observed. Hence it was concluded that the antiviral factor is not an interferon and its mechanism of action is different from that of an interferon.

e. The antiviral factor is probably not a degradative enzyme. The site and mode of action of the antiviral factor is still not known. In order to clarify these questions, further studies must be carried out with different viruses. One simple experiment was performed to test whether the factor is an enzyme that degrades viruses, e.g., a proteolytic enzyme. For this purpose, VSV was incubated with serial twofold dilutions of the factor for different time periods at 37° C. Bovine MDBK cells were then added to the wells and the extent of CPE was determined. It was found that VSV gave the same extent of CPE when mixed with the cells immediately after addition of the antiviral factor or when pre-incubated with the antiviral factor for 5 hrs at 37° C. Hence it was concluded that the antiviral factor is probably not a virus degrading enzyme.

TABLE 2

Sensitivity of the antiviral factor to heat and trypsin

| Sample | Activity U/ml | % |
|---|---|---|
| Stock (MONO Q) antiviral factor, overnight, room temp. | 75 | 100 |
| Stock antiviral factor + trypsin, overnight, room temp. | 25 | 33 |
| Stock antiviral factor (MONO Q), room temp., 10 min. | 65 | 100 |
| Stock antiviral factor, 100° C., 10 min. | 0 | 0 |

3.3 Size Exclusion Chromatography of the Antiviral Factor

Figure 9:
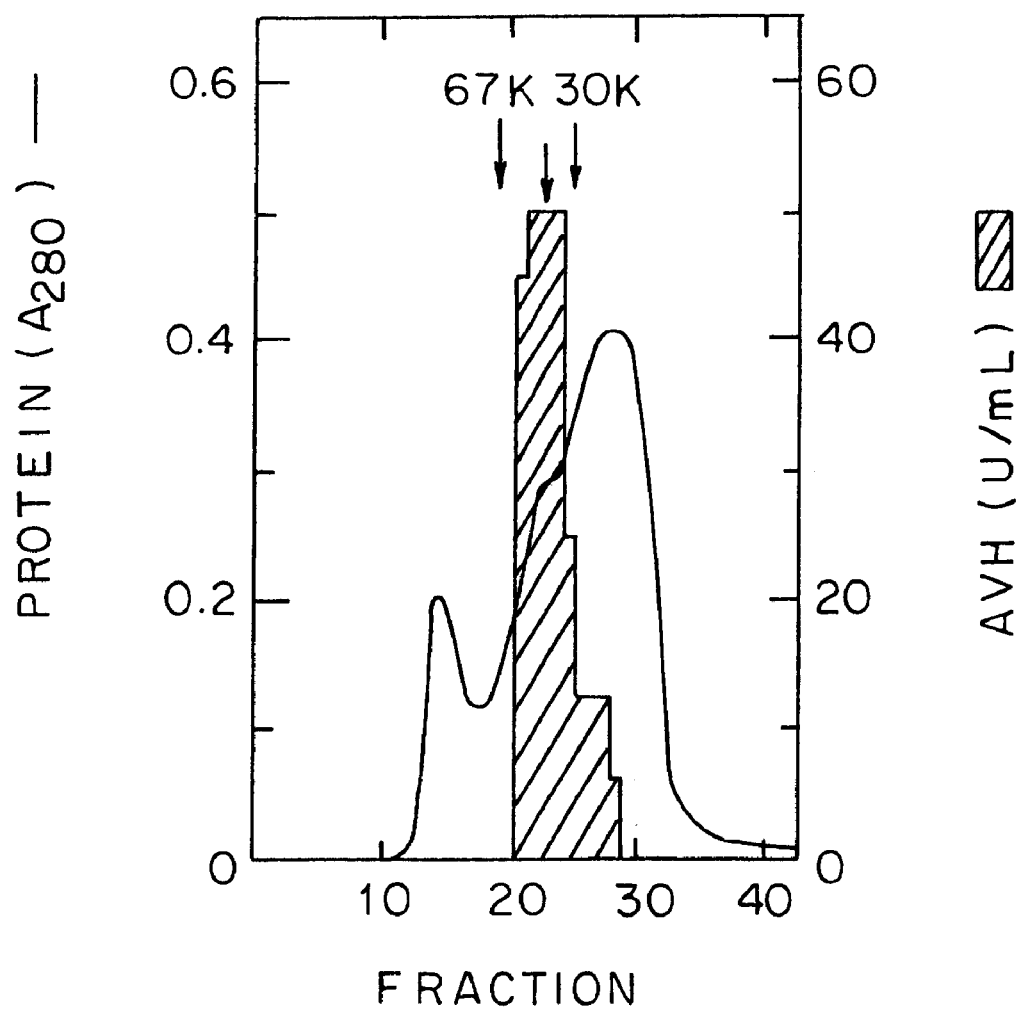
FIG. 9 shows the elution pattern of antiviral activity from a SUPEROSE 12 size exclusion HPLC column.

Antiviral factor from the TSK-DEAE step (0.4 ml) was fractionated on a size exclusion column (SUPEROSE 12, 1×30 cm, Pharmacia) in phosphate buffered saline under near physiological conditions. The column was pre-equilibrated and eluted with phosphate buffered saline at a flow rate of 0.5 ml/min. Fractions of 1 ml were collected and antiviral activity was measured in each fraction. The column was monitored at 280 nm (FIG. 9). The column was calibrated with bovine serum albumin (67K) and carbonic anhydrase (30K) as molecular weight markers. It was found that the antiviral activity eluted as a peak of apparent molecular weight 40,000. However, this peak was rather broad.

3.4 Species Specificity of the Antiviral Factor

The antiviral factor was found to be active on human WISH cells. It was also found to be active on bovine NDBK cells and murine L cells. Hence it was concluded that the factor is not species specific.

3.5 Protein Sequence Analysis and Identification of the Antiviral Factor

Aliquots (400 µl) of fractions 10–12 from the last RP-HPLC step (see 2.7 in example 2) were pooled, concentrated by ultrafiltration and the concentrate (0.5 µg) was subjected to microsequence analysis on model 475 protein microsequences (Applied Biosystems, USA). The resulting sequence of the N-terminal 15 amino acid residues (SEQ ID NO:1) as identified by this system is given in FIG. 10. The amino acid in cycle 10 was not identified while the Pro in cycle 3 and 15 was identified with relatively low confidence (given in Pmol ratio).

The resulting amino acid sequence (SEQ ID NO:1) was compared with NBRF protein databank and it gave 100% identity with the N-terminal sequence of the human low density lipoprotein (LDL) receptor (SEQ ID NO:2) starting at residue 25 of the precursor LDL receptor (residue 4 of mature LDL receptor). The amino acids in cycles 3, 10 and 15 were not intially identified due to the limitations of the sequencing method, but were later confirmed to be cysteine residues by homology with the mature LDL receptor sequence of FIG. 15 (SEQ ID NO:4). The identity between the isolated receptor and the known LDL receptor is shown in FIG. 11.

The soluble antiviral protein of the present invention has a molecular weight of between 29,000 or 40,000 according to the two methods that were used for its estimation. It is therefore concluded that the antiviral protein corresponds to the N-terminal cysteine-rich domain of the LDL receptor. According to Esser (Esser, V. et al. (1988) J. Biol. Chem. 263, 13282–13290) the cysteine-rich N-terminal domain of 292 amino acid residues is the ligand binding domain of LDL receptor and its calculated molecular weight is about 33,000–38,000 depending on the extent of glycosylation.

Example 4

Immunoaffinity Chromatography of the Antiviral Factor

Figure 12:
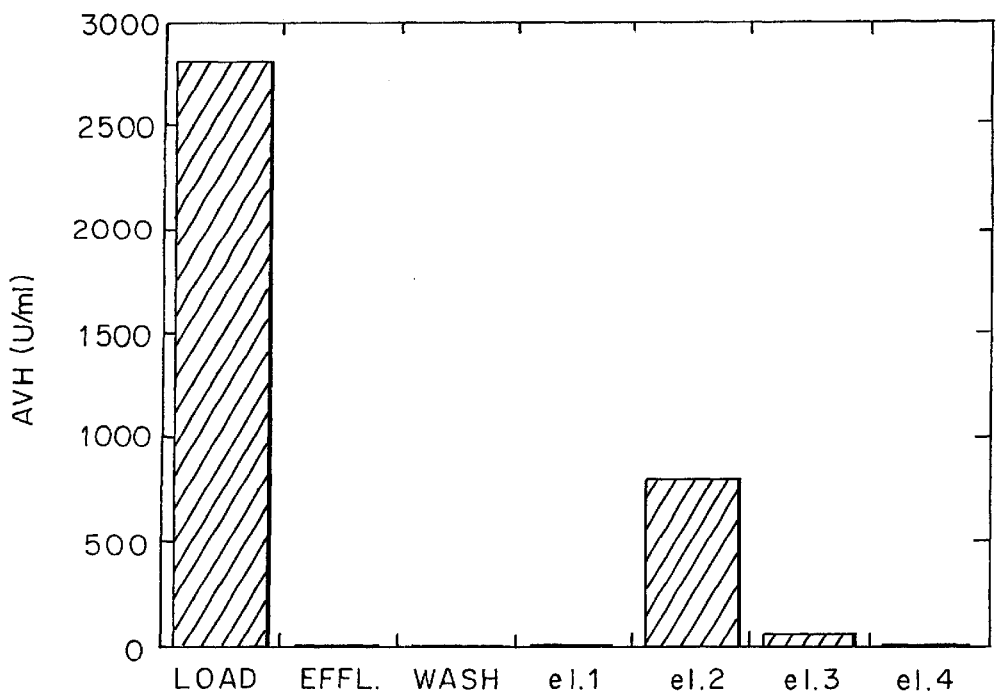
FIG. 12 shows the total antiviral activity of various fractions from the immunoaffinity chromatography of partially purified soluble LDL receptor on monoclonal antibody C7 column. The bars are: load-column load; eff1.–effluent (unbound fraction); el-1–4 elutions 1–4.
Figure 13:
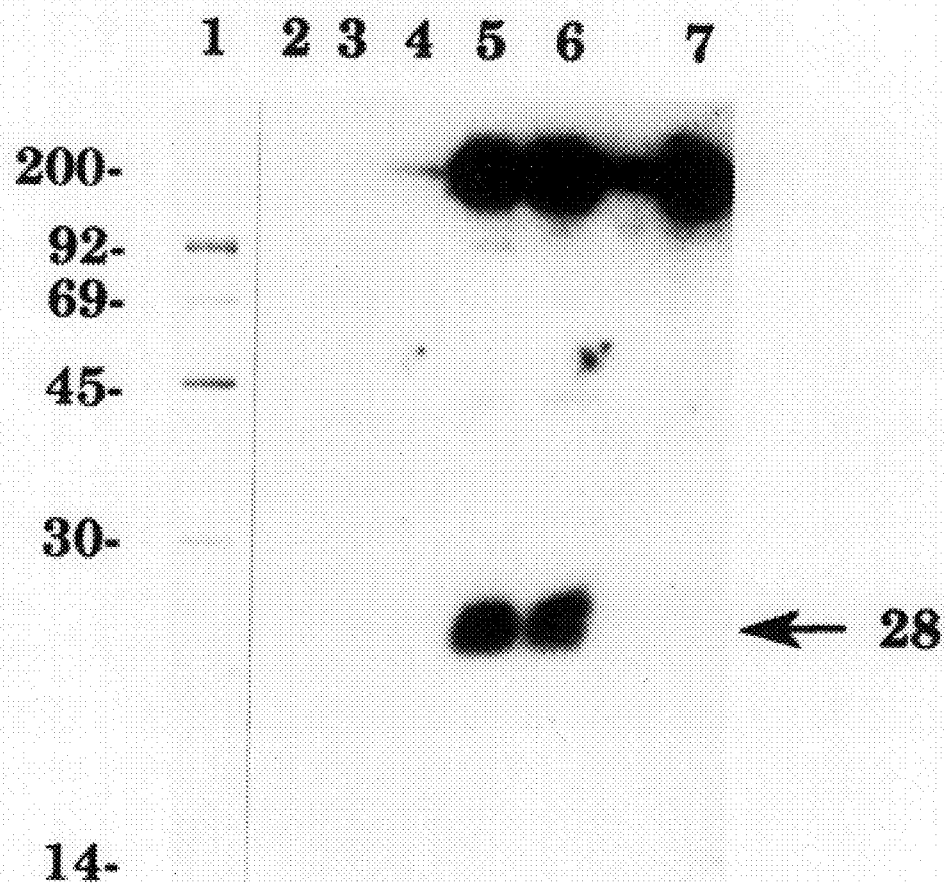
FIG. 13 shows a Western immunoblotting analysis of the various fractions from the immunoaffinity chromatography (shown in FIG. 12). The proteins were electroblotted to nitrocellulose and visualized with monoclonal antibody C7 and $^{125}$I-protein A. Lanes: 1. Molecular weight markers; 2.load; 3. unbound; 4. wash; 5. elution 2; 6. elution 3; 7. monoclonal antibody C7.

The most direct proof of identity of the antiviral factor and sLDLR was obtained by affinity chromatography of the crude antiviral protein on a monoclonal antibody C7 column. This antibody is directed against the ligand binding domain of bovine and human LDLR (Beisiegel, U. et al. (1981) J. Biol. Chem., 256, 11923–11931). Hybridoma C7 (ATCC, CRL 1691) was grown as ascites in mice and immunoglobulin was isolated from the ascitic fluid by ammonium sulfate fractionation. The C7 immunoglobulin (19 mg), was coupled to 1 ml agarose. Partially purified AVH from the 200 mM NaCl fraction of the TSK-DEAE step ("load", 14 ml, 37.8 mg protein, 2800 units) was loaded on the column; the effluent ("effl.") was collected and the column was washed ("wash") with a 70 ml of 0.5M NaCl in phosphate buffered saline (PBS) followed by PBS (30 ml). The column was then eluted with 50 mM $Na_2CO_3$ (pH 11) (el.2 and el.3) with a recovery of 32% (FIG. 12). The amount of protein in the eluted fractions was 0.15 mg and the degree of purification was 83. SDS-PAGE and silver staining gave many bands. However, on Western blotting (FIG. 13), with mAb C7 (gel run under non-reducing conditions) no receptor was detected in the load, effluent and wash fractions (lanes 2, 3 and 4, respectively). However, the 28K band of the soluble LDL receptor was obtained in el.2 and el.3, (lanes 5 and 6). Also higher molecular weight bands were seen in el.2 and el.3, including weak 40K and 100K bands which probably are larger extracellular fragments of the LDL receptor. The strong band near 200K is probably monoclonal antibody C7 which leaked from the column and reacted with protein A, as it was identical with a C7 sample (lane 7).

Example 5

Induction of Cell Surface LDLR by Interferons

Figure 14:
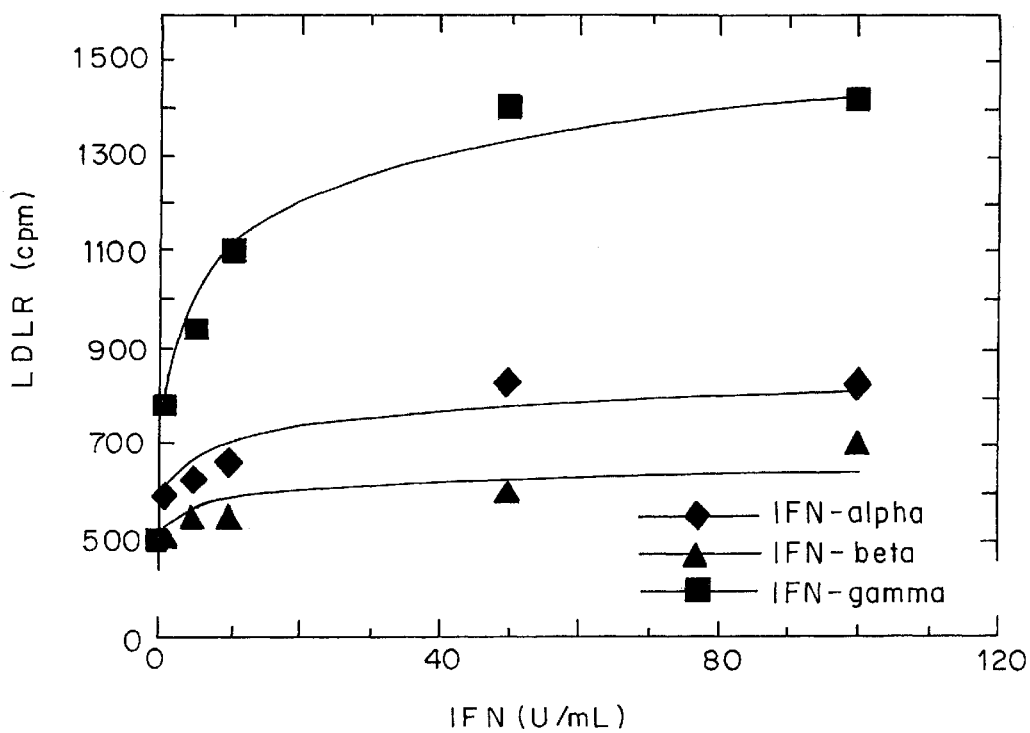
FIG. 14 shows a dose response induction of cell surface LDL receptor in WISH cells by various interferons. Cells were incubated with interferons for 19 hrs in medium containing 2% fetal calf serum and the level of cell surface LDL receptor was then determined by monoclonal antibody C7 and $^{125}$I-protein A.

The ability of interferon to induce soluble LDL receptor suggests that it can also induce cell surface LDL receptor, since both receptor forms share the same gene. To study the possible induction of the full size LDL receptor WISH cells grown to confluence in 1.7 cm wells were incubated with various interferons in medium containing 2% fetal bovine serum. The cells were washed, incubated with monoclonal antibody C7 from 2 hr at 4° C., washed, incubated with $^{125}$I-protein A (about 80,000 dpm) for 2 hr at 4° C., washed, harvested with trypsin and counted. In a time course experiment it was found that maximal induction of LDL receptor with interferon-γ (100 U/ml) occurred between 5 and 23 hr. A dose response study was then performed by incubating WISH cells for 19 hr with different interferons. It was found that interferon γ was the most potent inducer of LDL receptor and maximal induction was seem with 10–50 U/ml. Interferon alpha was a much weaker inducer while interferon beta probably did not induce LRL receptor at all (FIG. 14). The induction of LDL receptor as well as its basal level were abolished in the presence of the protein synthesis inhibitor cycloheximide.

Example 6

Isolation and Purification of Soluble LDL Receptor from Urine 6.1 Preparation of the Urine Concentrate A pool of 500 liter urine from healthy menopausal women was subjected to microfiltration on a PELLICON membrane with a pore size of 0.45 μm. The filtrate was concentrated by ultrafiltration using a PELLICON membrane with a molecular weight cut off of 10 K to a final volume of 700 ml. The concentrate was dialyzed against phosphate buffered saline containing 1 mM benzamidine and 0.1% sodium azide.

6.2 Affinity Chromatography of Soluble LDL Receptor with Monoclonal Antibodies

Antibodies against LDL receptor are utilized for the purification of the soluble fragment by affinity chromatography. The monoclonal antibody C7 (ATCC, CRL 1691) was used in this example for affinity chromatography. Ascitic fluid containing the monoclonal antibody secreted by hybridoma C7 was purified by ammonium sulfate precipitation at 50% saturation followed by extensive dialysis against PBS. About 10 mg of immunoglobulin were bound to 1 ml polyacrylhydrazide agarose as specified by Wilchek and Miron, *Methods in Enzymology*, 34:72076, 1979. Concentrated human urinary proteins (23 g in 730 ml, equivalent to 500 l of crude urine) were loaded on 1.0 ml of the C7 anti-LDL receptor antibody column at 4° C. at a flow rate of 0.25 ml/min. The column was washed with PBS until no protein was detected in the washing. Soluble LDL receptor was eluted by 50 mM $Na_2CO_3$ buffer, pH 11.5, containing 1 mM benzamidine and 0.02% $NaN_3$ (8×1 column volume fractions) and immediately neutralized by 3 M acetic acid. Antiviral activity was measured in the eluted fractions and 50,000 units were found in elution fractions no. 2 and 3. The total amount of protein in these fractions was 120 micrograms.

6.3 Reversed Phase HPLC

Figure 16:
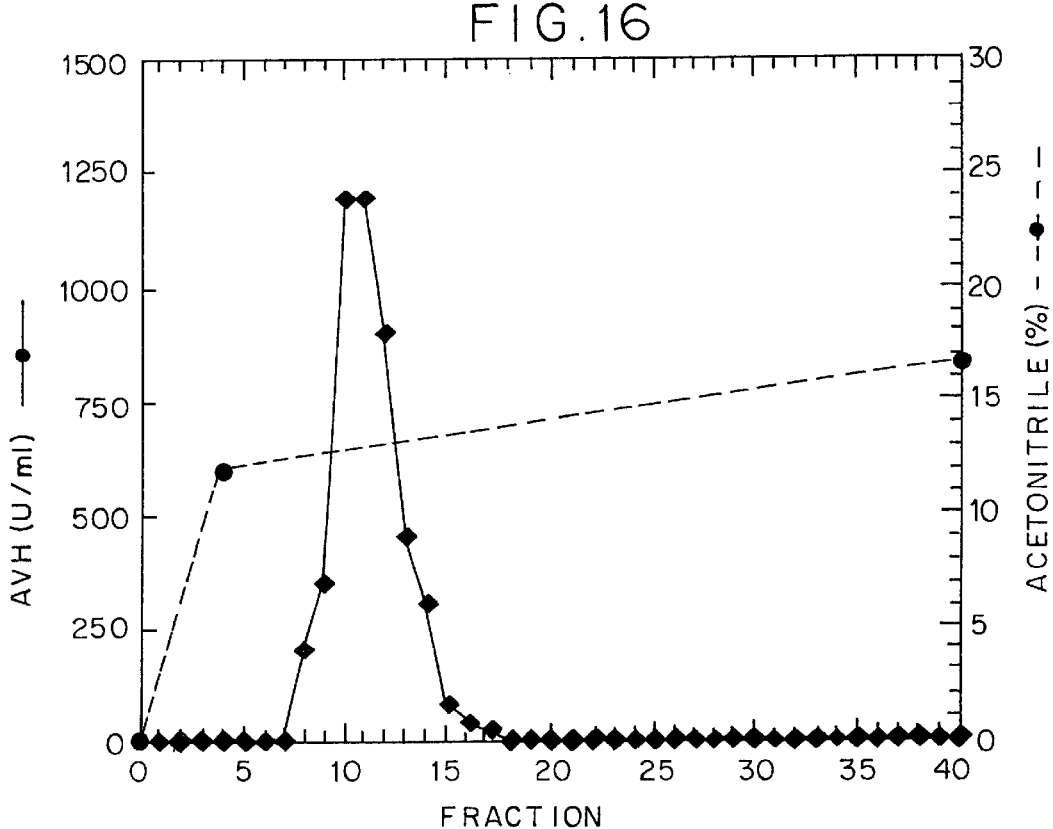
FIG. 16 shows the reversed-phase HPLC of affinity purified urinary soluble LDL receptor. Antiviral activity (AVH) and percentage acetonitrile are indicated.

An aliquot of soluble LDL-R from the affinity chromatography step in 6.2 (32 μg, 8800 units) was loaded on an AQUAPORE RP-300 RP-HPLC column (4.6×30 mm) that was preequilibrated with 20 mM Hepes buffer pH 7.5. The column was washed and eluted at a flow rate of 0.5 ml/min by an acetonitrile gradient in the same buffer. Fractions of 1 ml were collected and tested for antiviral activity. The antiviral activity eluted at 14% acetonitrile (FIG. 16). The column was monitored by flourescamine-based post-column reaction system (Stein S. and Moschera J. (1981) *Methods in Enzymology*, 79:7–16).

Figure 17:
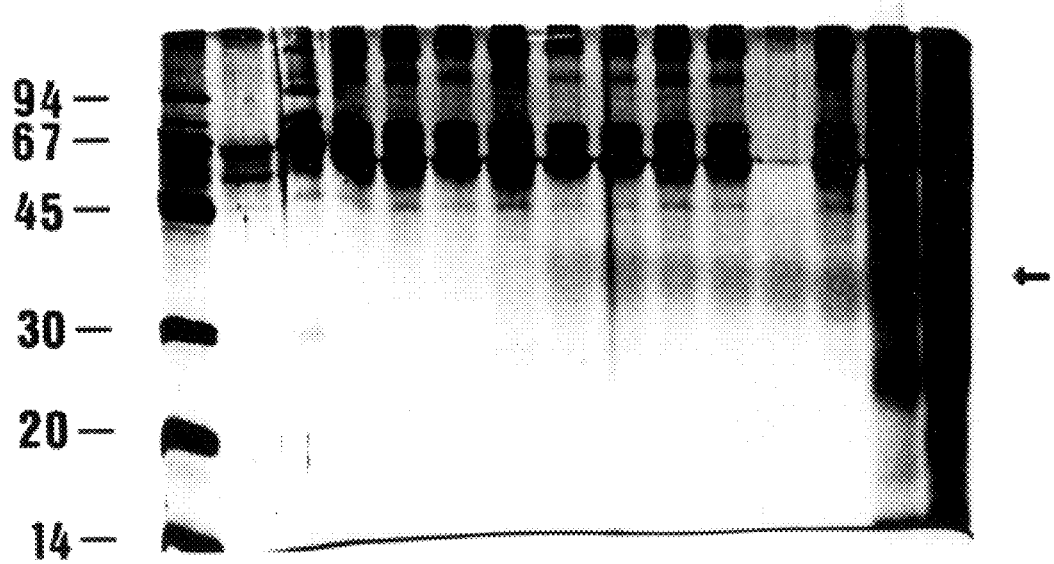
FIG. 17 shows the SDS-PAGE of aliquots of RP-HPLC fractions of FIG. 16.

Aliquots (30 μl) of each fraction were subjected to polyacrylamide (12%) gel electrophoresis in the presence of sodium dodecyl sulfate (SDS-PAGE) (FIG. 17). The protein bands were visualized by silver staining. The lanes (FIG. 17) are: 1. crude urinary proteins; 2. column load (C7 eluate); 3–12. HPLC fractions 9–18 respectively; 13. HPLC fraction 20; 14. control sample buffer; 15. molecular weight markers, indicated on the left side (FIG. 17).

Example 7

Size Exclusion Chromatography of Urinary Soluble LDL Receptor

Figure 18:
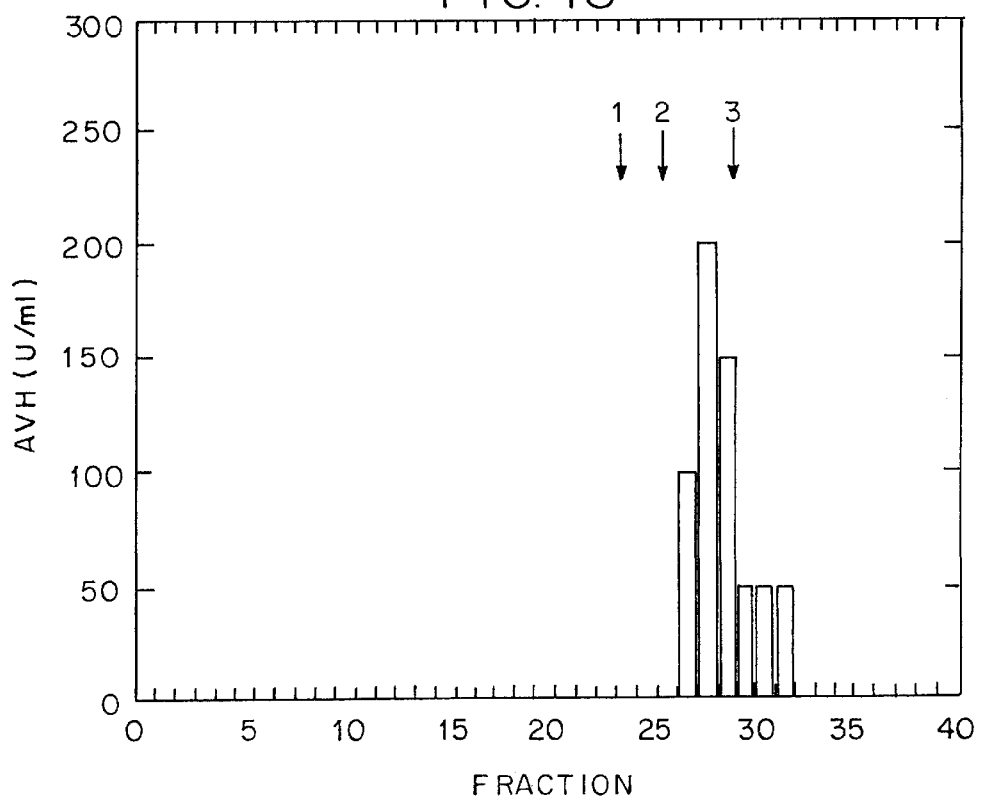
FIG. 18 shows size exclusion chromatography of an aliquot of the affinity-purified urinary soluble LDL receptor. Molecular weight markers elute at the indicated positions: (1) human immunoglobulin (150 kd); (2) bovine serum albumin (67 kd); (3) carbonic anhydrase (30 kd).

Soluble LDL receptor from the affinity chromatography step (1.5 μg, 200 units) was mixed with bovine serum albumin (200 μg), human immunoglobulin (200 μg) in phosphate buffered saline (200 μl total). The mixture was fractionated on a size exclusion column (SUPEROSE 12, 1×30 cm, Pharmacia) in phosphate buffered saline under near physiological conditions. The column was pre-equilibrated and eluted with phosphate buffered saline at a flow rate of 0.5 ml/min. Fractions of 0.5 ml were collected and antiviral activity was measured in each fraction. The column was monitored at 280 nm (FIG. 18). The column was calibrated with human immunoglobulin (150 K), bovine serum albumin (67 K) and carbonic anhydrase (30 K) as molecular weight markers. It was found that the antiviral activity eluted as a peak of apparent molecular weight 30,000, as a range of 26K–34K (FIG. 18).

Example 8

Protein Sequence Analysis and Identification of the Antiviral Factor

Fraction 10 from the RP-HPLC step (1 μg, see 6.3) was absorbed on a PVDF membrane (Prospin, Applied Biosystems, USA) and subjected to microsequence analysis on model 475 protein microsequencer (Applied Biosystems, USA). The resulting sequence of the N-terminal 16 amino acid residues (SEQ ID NO:5) was identified by this system. The amino acids in cycle 3, 10 and 15 were not initially identified, as would be expected for cys residues, but by comparison with the sequence of the human LDL receptor which has cys residues in these positions, these amino acids are cys residues. As can be seen from FIG. 19, the sequence (SEQ ID NO:5) corresponded to a portion of the first fifty residues of the human LDL receptor (SEQ ID NO:2). Thus, the N-terminal sequence of soluble LDL receptor (SEQ ID NO:6) is as shown in SEQ ID NO:5 with cysteine residue at the 3, 10, and 15 positions.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A substantially purified protein which inhibits viral infection of mammalian cells and which has the amino acid sequence and at least the decree of purity of the protein produced by the process comprising:

growing human WISH cells in culture;

reducing the cells with IFN-gamma in a serum-free medium and harvesting the culture supernatant;

concentrating said supernatant by ultrafiltration with a membrane of molecular weight cut-off of about 10,000 Da;

subjecting said concentrated supernatant to ion exchange chromatography and selecting the fractions exhibiting inhibition of the vesicular stomatitis virus (VSV)-induced cytopathic effect in WISH cells;

applying said selected fraction to reversed phase high pressure liquid chromatography (RP-HPLC) at about neutral pH and recovering the fractions exhibiting inhibition of the VSV-induced cytopathic effect in WISH cells; and recovering protein from said selected RP-HPLC fraction, said protein being a substantially purified protein of apparent molecular weight of 40,000 Da by size exclusion chromatography which inhibits viral infection of mammalian cells.

2. A composition in accordance with claim 1 wherein said protein has an amino acid sequence which begins at residue 4 and ending at a residue between 292–352, inclusive, of SEQ ID NO:4.

3. An antiviral pharmaceutically acceptable composition consisting essentially of an antiviral effective amount of an antiviral active principle and a pharmaceutically acceptable carrier, wherein said active principle comprises a protein in accordance with claim 1.

4. An antiviral pharmaceutically acceptable composition according to claim 3, wherein said active principle is a combination of said protein and an antiviral agent other than said protein.

5. An antiviral pharmaceutically acceptable composition according to claim 4, wherein said antiviral agent other than said protein is an interferon.

6. An antiviral pharmaceutically acceptable composition consisting essentially of an antiviral effective amount of an antiviral active principle and a pharmaceutically acceptable carrier, wherein said active principle comprises a soluble LDL receptor protein comprising the amino acid sequence 4 to 292 of SEQ ID NO:4 and an antiviral agent other than said soluble LDL receptor protein.

7. An antiviral pharmaceutical composition according to claim 6 wherein said antiviral agent other than said soluble LDL receptor protein is an interferon.

8. A substantially purified protein which inhibits viral infection of mammalian cells and which has the amino acid sequence and at least the degree of purity of the protein provided by the process comprising:

filtering human urine through a membrane with a molecular weight cut-off of 10 K;

subjecting the filtrate from said filtering step to affinity chromatography using an antibody against LDL receptor and retaining the fractions having antiviral activity; and subjecting the fractions obtained from said subjecting step to reversed phase high pressure liquid chromatography (RP-HPLC) with an acetonitrile gradient in a buffer of pH 7.5 and collecting the elution fraction having antiviral activity; and recovering protein from said selected RP-HPLC fraction, said protein being a substantially purified protein of apparent molecular weight of about 30 K, and having an N-terminal amino acid sequence of SEQ ID NO:5.

9. A polypeptide consisting of a mutein or fragment of the soluble LDL receptor protein consisting of the amino acid sequence 4 to 292 of SEQ ID NO:4, which mutein or fragment is a mutein which differs from said sequence of the soluble LDL receptor protein by adding, substituting or deleting 1–10 residues thereof, and retains antiviral activity, or a fragment which is an active fragment of said soluble LDL receptor protein or said mutein, which active fragment retains antiviral activity, or a pharmaceutically acceptable salt or functional derivative of said mutein or fragment.

10. An antiviral pharmaceutically acceptable composition consisting essentially of an antiviral effective amount of an antiviral active principle and a pharmaceutically acceptable carrier, wherein said active principle comprises a polypeptide in accordance with claim 9.

11. A polypeptide consisting of a mutein or fragment of the protein defined in claim 1, which mutein or fragment is a mutein which differs from the sequence of said protein by adding, substituting or deleting one residue thereof, and retains antiviral activity, or a salt or functional derivative of said mutein, or a fragment which is an active fragment of said protein or said mutein, which active fragment retains antiviral activity.

12. A substantially purified protein which is a salt or functional derivative of the protein defined in claim 1.

* * * * *

UNITED STATES PATENT AND TRADEMARK OFFICE
CERTIFICATE OF CORRECTION

| | | |
|---|---|---|
| PATENT NO. | : 6,365,713 B1 | |
| DATED | : April 2, 2002 | |
| INVENTOR(S) | : Menachem Rubinstein, Daneila Novick, Nathan Tal and Dina G. Fischer | |

It is certified that error appears in the above-identified patent and that said Letters Patent is hereby corrected as shown below:

<u>Column 36,</u>
Line 26, delete "decree" and insert therefor -- degree --.

<u>Column 37,</u>
Line 29, delete "reducing" and insert therefor -- inducing --.
Line 51, delete "292-352" and insert therefor --292-350 --.

Signed and Sealed this

Fourth Day of June, 2002

Attest:

JAMES E. ROGAN
Attesting Officer    *Director of the United States Patent and Trademark Office*

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 15 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

```
Asp Arg Pro Glu Arg Asn Glu Phe Gln Xaa Gln Asp Gly Lys Pro
1               5                   10                  15
```

(2) INFORMATION FOR SEQ ID NO:2:

(i) SEQUENCE CHARACTERISTICS:
       (A) LENGTH: 50 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:2:

```
Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
                20                  25                  30

Gln Cys Gln Asp Gly Lys Cys Ile Ser Tyr Lys Trp Val Cys Asp Gly
            35                  40                  45

Ser Ala
    50
```

(2) INFORMATION FOR SEQ ID NO:3:

(i) SEQUENCE CHARACTERISTICS:
       (A) LENGTH: 5095 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 14..2593

(ix) FEATURE:
       (A) NAME/KEY: mat_peptide
       (B) LOCATION: 77..2593

(xi) SEQUENCE DESCRIPTION: SEQ ID NO:3:

```
AGAGGCTGCG AGC ATG GGG CCC TGG GGC TGG AAA TTG CGC TGG ACC GTC        49
           Met Gly Pro Trp Gly Trp Lys Leu Arg Trp Thr Val
           -21 -20             -15                 -10

GCC TTG CTC CTC GCC GCG GCG GGG ACT GCA GTG GGC GAC AGA TGT GAA       97
Ala Leu Leu Leu Ala Ala Ala Gly Thr Ala Val Gly Asp Arg Cys Glu
             -5                   1                   5

AGA AAC GAG TTC CAG TGC CAA GAC GGG AAA TGC ATC TCC TAC AAG TGG      145
Arg Asn Glu Phe Gln Cys Gln Asp Gly Lys Cys Ile Ser Tyr Lys Trp
```

|                                                                                  |      |
|----------------------------------------------------------------------------------|------|
| GTC TGC GAT GGC AGC GCT GAG TGC CAG GAT GGC TCT GAT GAG TCC CAG                   | 193  |
| Val Cys Asp Gly Ser Ala Glu Cys Gln Asp Gly Ser Asp Glu Ser Gln                   |      |
|      25                  30                  35                                  |      |
| GAG ACG TGC TTG TCT GTC ACC TGC AAA TCC GGG GAC TTC AGC TGT GGG                   | 241  |
| Glu Thr Cys Leu Ser Val Thr Cys Lys Ser Gly Asp Phe Ser Cys Gly                   |      |
|  40                  45                  50                  55                  |      |
| GGC CGT GTC AAC CGC TGC ATT CCT CAG TTC TGG AGG TGC GAT GGC CAA                   | 289  |
| Gly Arg Val Asn Arg Cys Ile Pro Gln Phe Trp Arg Cys Asp Gly Gln                   |      |
|              60                  65                  70                          |      |
| GTG GAC TGC GAC AAC GGC TCA GAC GAG CAA GGC TGT CCC CCC AAG ACG                   | 337  |
| Val Asp Cys Asp Asn Gly Ser Asp Glu Gln Gly Cys Pro Pro Lys Thr                   |      |
|                  75                  80                  85                      |      |
| TGC TCC CAG GAC GAG TTT CGC TGC CAC GAT GGG AAG TGC ATC TCT CGG                   | 385  |
| Cys Ser Gln Asp Glu Phe Arg Cys His Asp Gly Lys Cys Ile Ser Arg                   |      |
|          90                  95                  100                             |      |
| CAG TTC GTC TGT GAC TCA GAC CGG GAC TGC TTG GAC GGC TCA GAC GAG                   | 433  |
| Gln Phe Val Cys Asp Ser Asp Arg Asp Cys Leu Asp Gly Ser Asp Glu                   |      |
|              105                 110                 115                         |      |
| GCC TCC TGC CCG GTG CTC ACC TGT GGT CCC GCC AGC TTC AGT GCA AAC                   | 481  |
| Ala Ser Cys Pro Val Leu Thr Cys Gly Pro Ala Ser Phe Gln Cys Asn                   |      |
| 120                 125                 130                 135                  |      |
| AGC TCC ACC TGC ATC CCC CAG CTG TGG GCC TGC GAC AAC GAC CCC GAC                   | 529  |
| Ser Ser Thr Cys Ile Pro Gln Leu Trp Ala Cys Asp Asn Asp Pro Asp                   |      |
|                 140                 145                 150                      |      |
| TGC GAA GAT GGC TCG GAT GAG TGG CCG CAG CGC TGT AGG GGT CTT TAC                   | 577  |
| Cys Glu Asp Gly Ser Asp Glu Trp Pro Gln Arg Cys Arg Gly Leu Tyr                   |      |
|         155                 160                 165                              |      |
| GTG TTC CAA GGG GAC AGT AGC CCC TGC TCG GCC TTC GAG TTC CAC TGC                   | 625  |
| Val Phe Gln Gly Asp Ser Ser Pro Cys Ser Ala Phe Glu Phe His Cys                   |      |
|             170                 175                 180                          |      |
| CTA AGT GGC GAG TGC ATC CAC TCC AGC TGG CGC TGT GAT GGT GGC CCC                   | 673  |
| Leu Ser Gly Glu Cys Ile His Ser Ser Trp Arg Cys Asp Gly Gly Pro                   |      |
|         185                 190                 195                              |      |
| GAC TGC AAG GAC AAA TCT GAC GAG GAA AAC TGC GCT GTG GCC ACC TGT                   | 721  |
| Asp Cys Lys Asp Lys Ser Asp Glu Glu Asn Cys Ala Val Ala Thr Cys                   |      |
| 200                 205                 210                 215                  |      |
| CGC CCT GAC GAA TTC CAG TGC TCT GAT GGA AAC TGC ATC CAT GGC AGC                   | 769  |
| Arg Pro Asp Glu Phe Gln Cys Ser Asp Gly Asn Cys Ile His Gly Ser                   |      |
|                 220                 225                 230                      |      |
| CGG CAG TGT GAC CGG GAA TAT GAC TGC AAG GAC ATG AGC GAT GAA GTT                   | 817  |
| Arg Gln Cys Asp Arg Glu Tyr Asp Cys Lys Asp Met Ser Asp Glu Val                   |      |
|             235                 240                 245                          |      |
| GGC TGC GTT AAT GTG ACA CTC TGC GAG GGA CCC AAC AAG TTC AAG TGT                   | 865  |
| Gly Cys Val Asn Val Thr Leu Cys Glu Gly Pro Asn Lys Phe Lys Cys                   |      |
|         250                 255                 260                              |      |
| CAC AGC GGC GAA TGC ATC ACC CTG GAC AAA GTC TGC AAC ATG GCT AGA                   | 913  |
| His Ser Gly Glu Cys Ile Thr Leu Asp Lys Val Cys Asn Met Ala Arg                   |      |
|     265                 270                 275                                  |      |
| GAC TGC CGG GAC TGG TCA GAT GAA CCC ATC AAA GAG TGC GGG ACC AAC                   | 961  |
| Asp Cys Arg Asp Trp Ser Asp Glu Pro Ile Lys Glu Cys Gly Thr Asn                   |      |
| 280                 285                 290                 295                  |      |
| GAA TGC TTG GAC AAC AAC GGC GGC TGT TCC CAC GTC TGC AAT GAC CTT                   | 1009 |
| Glu Cys Leu Asp Asn Asn Gly Gly Cys Ser His Val Cys Asn Asp Leu                   |      |
|                 300                 305                 310                      |      |
| AAG ATC GGC TAC GAG TGC CTG TGC CCC GAC GGC TTC CAG CTG GTG GCC                   | 1057 |
| Lys Ile Gly Tyr Glu Cys Leu Cys Pro Asp Gly Phe Gln Leu Val Ala                   |      |
|             315                 320                 325                          |      |
| CAG CGA AGA TGC GAA GAT ATC GAT GAG TGT CAG GAT CCC GAC ACC TGC                   | 1105 |

```
                                                              -continued

Gln Arg Arg Cys Glu Asp Ile Asp Glu Cys Gln Asp Pro Asp Thr Cys
            330                 335                 340

AGC CAG CTC TGC GTG AAC CTG GAG GGT GGC TAC AAG TGC CAG TGT GAG           1153
Ser Gln Leu Cys Val Asn Leu Glu Gly Gly Tyr Lys Cys Gln Cys Glu
345                 350                 355

GAA GGC TTC CAG CTG GAC CCC CAC ACG AAG GCC TGC AAG GCT GTG GGC           1201
Glu Gly Phe Gln Leu Asp Pro His Thr Lys Ala Cys Lys Ala Val Gly
360                 365                 370                 375

TCC ATC GCC TAC CTC TTC TTC ACC AAC CGG CAC GAG GTC AGG AAG ATG           1249
Ser Ile Ala Tyr Leu Phe Phe Thr Asn Arg His Glu Val Arg Lys Met
                380                 385                 390

ACG CTG GAC CGG AGC GAG TAC ACC AGC CTC ATC CCC AAC CTG AGG AAC           1297
Thr Leu Asp Arg Ser Glu Tyr Thr Ser Leu Ile Pro Asn Leu Arg Asn
                395                 400                 405

GTG GTC GCT CTG GAC ACG GAG GTG GCC AGC AAT AGA ATC TAC TGG TCT           1345
Val Val Ala Leu Asp Thr Glu Val Ala Ser Asn Arg Ile Tyr Trp Ser
            410                 415                 420

GAC CTG TCC CAG AGA ATG ATC TGC AGC ACC CAG CTT GAC AGA GCC CAC           1393
Asp Leu Ser Gln Arg Met Ile Cys Ser Thr Gln Leu Asp Arg Ala His
        425                 430                 435

GGC GTC TCT TCC TAT GAC ACC GTC ATC AGC AGG GAC ATC CAG GCC CCC           1441
Gly Val Ser Ser Tyr Asp Thr Val Ile Ser Arg Asp Ile Gln Ala Pro
440                 445                 450                 455

GAC GGG CTG GCT GTG GAC TGG ATC CAC AGC AAC ATC TAC TGG ACC GAC           1489
Asp Gly Leu Ala Val Asp Trp Ile His Ser Asn Ile Tyr Trp Thr Asp
                460                 465                 470

TCT GTC CTG GGC ACT GTC TCT GTT GCG GAT ACC AAG GGC GTG AAG AGG           1537
Ser Val Leu Gly Thr Val Ser Val Ala Asp Thr Lys Gly Val Lys Arg
                475                 480                 485

AAA ACG TTA TTC AGG GAG AAC GGC TCC AAG CCA AGG GCC ATC GTG GTG           1585
Lys Thr Leu Phe Arg Glu Asn Gly Ser Lys Pro Arg Ala Ile Val Val
            490                 495                 500

GAT CCT GTT CAT GGC TTC ATG TAC TGG ACT GAC TGG GGA ACT CCC GCC           1633
Asp Pro Val His Gly Phe Met Tyr Trp Thr Asp Trp Gly Thr Pro Ala
        505                 510                 515

AAG ATC AAG AAA GGG GGC CTG AAT GGT GTG GAC ATC TAC TCG CTG GTG           1681
Lys Ile Lys Lys Gly Gly Leu Asn Gly Val Asp Ile Tyr Ser Leu Val
520                 525                 530                 535

ACT GAA AAC ATT CAG TGG CCC AAT GGC ATC ACC CTA GAT CTC CTC AGT           1729
Thr Glu Asn Ile Gln Trp Pro Asn Gly Ile Thr Leu Asp Leu Leu Ser
                540                 545                 550

GGC CGC CTC TAC TGG GTT GAC TCC AAA CTT CAC TCC ATC TCA AGC ATC           1777
Gly Arg Leu Tyr Trp Val Asp Ser Lys Leu His Ser Ile Ser Ser Ile
                555                 560                 565

GAT GTC AAT GGG GGC AAC CGG AAG ACC ATC TTG GAG GAT GAA AAG AGG           1825
Asp Val Asn Gly Gly Asn Arg Lys Thr Ile Leu Glu Asp Glu Lys Arg
            570                 575                 580

CTG GCC CAC CCC TTC TCC TTG GCC GTC TTT GAG GAC AAA GTA TTT TGG           1873
Leu Ala His Pro Phe Ser Leu Ala Val Phe Glu Asp Lys Val Phe Trp
        585                 590                 595

ACA GAT ATC ATC AAC GAA GCC ATT TTC AGT GCC AAC CGC CTC ACA GGT           1921
Thr Asp Ile Ile Asn Glu Ala Ile Phe Ser Ala Asn Arg Leu Thr Gly
600                 605                 610                 615

TCC GAT GTC AAC TTG TTG GCT GAA AAC CTA CTG TCC CCA GAG GAT ATG           1969
Ser Asp Val Asn Leu Leu Ala Glu Asn Leu Leu Ser Pro Glu Asp Met
                620                 625                 630

GTC CTC TTC CAC AAC CTC ACC CAG CCA AGA GGA GTG AAC TGG TGT GAG           2017
Val Leu Phe His Asn Leu Thr Gln Pro Arg Gly Val Asn Trp Cys Glu
                635                 640                 645
```

```
AGG ACC ACC CTG AGC AAT GGC GGC TGC CAG TAT CTG TGC CTC CCT GCC      2065
Arg Thr Thr Leu Ser Asn Gly Gly Cys Gln Tyr Leu Cys Leu Pro Ala
            650                 655                 660

CCG CAG ATC AAC CCC CAC TCG CCC AAG TTT ACC TGC GCC TGC CCG GAC      2113
Pro Gln Ile Asn Pro His Ser Pro Lys Phe Thr Cys Ala Cys Pro Asp
            665                 670                 675

GGC ATG CTG CTG GCC AGG GAC ATG AGG AGC TGC CTC ACA GAG GCT GAG      2161
Gly Met Leu Leu Ala Arg Asp Met Arg Ser Cys Leu Thr Glu Ala Glu
680                 685                 690                 695

GCT GCA GTG GCC ACC CAG GAG ACA TCC ACC GTC AGG CTA AAG GTC AGC      2209
Ala Ala Val Ala Thr Gln Glu Thr Ser Thr Val Arg Leu Lys Val Ser
            700                 705                 710

TCC ACA GCC GTA AGG ACA CAG CAC ACA ACC ACC CGG CCT GTT CCC GAC      2257
Ser Thr Ala Val Arg Thr Gln His Thr Thr Thr Arg Pro Val Pro Asp
            715                 720                 725

ACC TCC CGG CTG CCT GGG GCC ACC CCT GGG CTC ACC ACG GTG GAG ATA      2305
Thr Ser Arg Leu Pro Gly Ala Thr Pro Gly Leu Thr Thr Val Glu Ile
            730                 735                 740

GTG ACA ATG TCT CAC CAA GCT CTG GGC GAC GTT GCT GGC AGA GGA AAT      2353
Val Thr Met Ser His Gln Ala Leu Gly Asp Val Ala Gly Arg Gly Asn
            745                 750                 755

GAG AAG AAG CCC AGT AGC GTG AGG GCT CTG TCC ATT GTC CTC CCC ATC      2401
Glu Lys Lys Pro Ser Ser Val Arg Ala Leu Ser Ile Val Leu Pro Ile
760                 765                 770                 775

GTG CTC CTC GTC TTC CTT TGC CTG GGG GTC TTC CTT CTA TGG AAG AAC      2449
Val Leu Leu Val Phe Leu Cys Leu Gly Val Phe Leu Leu Trp Lys Asn
            780                 785                 790

TGG CGG CTT AAG AAC ATC AAC AGC ATC AAC TTT GAC AAC CCC GTC TAT      2497
Trp Arg Leu Lys Asn Ile Asn Ser Ile Asn Phe Asp Asn Pro Val Tyr
            795                 800                 805

CAG AAG ACC ACA GAG GAT GAG GTC CAC ATT TGC CAC AAC CAG GAC GGC      2545
Gln Lys Thr Thr Glu Asp Glu Val His Ile Cys His Asn Gln Asp Gly
            810                 815                 820

TAC AGC TAC CCC TCG AGA CAG ATG GTC AGT CTG GAG GAT GAC GTG GCG      2593
Tyr Ser Tyr Pro Ser Arg Gln Met Val Ser Leu Glu Asp Asp Val Ala
            825                 830                 835

TGAACATCTG CCTGGAGTCC CGCCCCTGCC CAGAACCCTT CCTGAGACCT CGCCGGCCTT   2653
GTTTTATTCA AAGACAGAGA AGACCAAAGC ATTGCCTGCC AGAGCTTTGT TTTATATATT   2713
TATTCATCTG GGAGGCAGAA CAGGCTTCGG ACAGTGCCCA TGCAATGGCT TGGGTTGGGA   2773
TTTTGGTTTC TTCCTTTCCT GTGAAGGATA AGAGAAACAG GCCCGGGGGG ACCAGGATGA   2833
CACCTCCATT TCTCTCCAGG AAGTTTTGAG TTTCTCTCCA CCGTGACACA ATCCTCAAAC   2893
ATGGAAGATG AAAGGGCAGG GGATGTCAGG CCCAGAGAAG CAAGTGGCTT TCAACACACA   2953
ACAGCAGATG GCACCAACGG GACCCCCTGG CCCTGCCTCA TCCACCAATC TCTAAGCCAA   3013
ACCCCTAAAC TCAGGAGTCA ACGTGTTTAC CTCTTCTATG CAAGCCTTGC TAGACAGCCA   3073
GGTTAGCCTT TGCCCTGTCA CCCCCGAATC ATGACCCACC CAGTGTCTTT CGAGGTGGGT   3133
TTGTACCTTC CTTAAGCCAG GAAAGGGATT CATGGCGTCG GAAATGATCT GGCTGAATCC   3193
GTGGTGGCAC CGAGACCAAA CTCATTCACC AAATGATGCC ACTTCCCAGA GGCAGAGCCT   3253
GAGTCACCGG TCACCCTTAA TATTTATTAA GTGCCTGAGA CACCCGGTTA CCTTGGCCGT   3313
GAGGACACGT GGCCTGCACC CAGGTGTGGC TGTCAGGACA CCAGCCTGGT GCCCATCCTC   3373
CCGACCCCTA CCCACTTCCA TTCCCGTGGT CTCCTTGCAC TTTCTCAGTT CAGAGTTGTA   3433
CACTGTGTAC ATTTGGCATT TGTGTTATTA TTTTGCACTG TTTTCTGTCG TGTGTGTTGG   3493
GATGGGATCC CAGGCCAGGG AAAGCCCGTG TCAATGAATG CCGGGGACAG AGAGGGGCAG   3553
```

-continued

```
GTTGACCGGG ACTTCAAAGC CGTGATCGTG AATATCGAGA ACTGCCATTG TCGTCTTTAT    3613

GTCCGCCCAC CTAGTGCTTC CACTTCTATG CAAATGCCTC CAAGCCATTC ACTTCCCCAA    3673

TCTTGTCGTT GATGGGTATG TGTTTAAAAC ATGCACGGTG AGGCCGGGCG CAGTGGCCTC    3733

ACGCCTGTAA TCCCAGCACT TTGGGAGGCC GAGGCGGGTG GATCATGAGG TCAGGAGATC    3793

GAGACCATCC TGGCTAACAA GGTGAAACCC CGTCTCTACT AAAAATACAA AAAATTAGCC    3853

GGGCGCGGTG GTGGGCACCT GTAGTCCCAG CTACTCGGGA GGCTGAGGCA GGAGAATGGT    3913

GTGAACCCGG GAAGCGGAGC TTGCAGTGAG CCGAGATTGC GCCACTGCAG TCCGCAGTCT    3973

GGCCTGGGCG ACAGAGCGAG ACTCCGTCTC AAAAAAAACA AAACAAAAAA AAACCATGCA    4033

TGGTGCATCA GCAGCCCATG GCCTCTGGCC AGGCATGGCG AGGCTGAGGT GGGAGGATGG    4093

TTTGAGCTCA GGCATTTGAG GCTGTCGTGA GCTATGATTA TGCCACTGCT TTCCAGCCTG    4153

GGCAACATAG TAAGACCCCA TCTCTTAAAA AATGAATTTG GCCAGACACA GGTGCCTCAC    4213

GCCTGTAATC CCAGCACTTT GGGAGGCTGA GCTGGATCAC TTGAGTTCAG GAGTTGGAGA    4273

CCAGGCCTGA GCAACAAAGC GAGATCCCAT CTCTACAAAA ACCAAAAAGT TAAAAATCAG    4333

CTGGGTATGG TGGCACGTGC CTGTGATCCC AGCTACTTGG GAGGCTGAGG CAGGAGGATC    4393

GCCTGAGCCC AGGAGGTGGA GGTTGCAGTG AGCCATGATC GAGCCACTGC ACTCCAGCCT    4453

GGGCAACAGA TGAAGACCCT ATTTCAGAAA TACAACTATA AAAAAAATAA ATAAATCCTC    4513

CAGTCTGGAT CGTTTGACGG GACTTCAGGT TCTTTCTGAA ATCGCCGTGT TACTGTTGCA    4573

CTGATGTCCG GAGAGACAGT GACAGCCTCC GTCAGACTCC CGCGTGAAGA TGTCACAAGG    4633

GATTGGCAAT TGTCCCCAGG GACAAAACAC TGTGTCCCCC CCAGTGCAGG GAACCGTGAT    4693

AAGCCTTTCT GGTTTCGGAG CACGTAAATG CGTCCCTGTA CAGATAGTGG GGATTTTTTG    4753

TTATGTTTGC ACTTTGTATA TTGGTTGAAA CTGTTATCAC TTATATATAT ATATACACAC    4813

ATATATATAA AATCTATTTA TTTTTGCAAA CCCTGGTTGC TGTATTTGTT CAGTGACTAT    4873

TCTCGGGGCC CTGTGTAGGG GGTTATTGCC TCTGAAATGC CTCTTCTTTA TGTACAAAGA    4933

TTATTTGCAC GAACTGGACT GTGTGCAACG CTTTTTGGGA GAATGATGTC CCCGTTGTAT    4993

GTATGAGTGG CTTCTGGGAG ATGGGTGTCA CTTTTTAAAC CACTGTATAG AAGGTTTTTG    5053

TAGCCTGAAT GTCTTACTGT GATCAATTAA ATTTCTTAAA TG    5095
```

(2) INFORMATION FOR SEQ ID NO:4:

(i) SEQUENCE CHARACTERISTICS:
       (A) LENGTH: 860 amino acids
       (B) TYPE: amino acid
       (D) TOPOLOGY: linear (ii) MOLECULE TYPE: protein (xi) SEQUENCE DESCRIPTION: SEQ ID NO:4:

```
Met Gly Pro Trp Gly Trp Lys Leu Arg Trp Thr Val Ala Leu Leu Leu
-21 -20              -15                 -10

Ala Ala Ala Gly Thr Ala Val Gly Asp Arg Cys Glu Arg Asn Glu Phe
 -5               1               5                  10

Gln Cys Gln Asp Gly Lys Cys Ile Ser Tyr Lys Trp Val Cys Asp Gly
                15              20              25

Ser Ala Glu Cys Gln Asp Gly Ser Asp Glu Ser Gln Glu Thr Cys Leu
            30              35              40

Ser Val Thr Cys Lys Ser Gly Asp Phe Ser Cys Gly Gly Arg Val Asn
        45              50              55
```

-continued

```
Arg Cys Ile Pro Gln Phe Trp Arg Cys Asp Gly Gln Val Asp Cys Asp
 60                  65                  70                  75

Asn Gly Ser Asp Glu Gln Gly Cys Pro Pro Lys Thr Cys Ser Gln Asp
             80                  85                  90

Glu Phe Arg Cys His Asp Gly Lys Cys Ile Ser Arg Gln Phe Val Cys
                 95                 100                 105

Asp Ser Asp Arg Asp Cys Leu Asp Gly Ser Asp Glu Ala Ser Cys Pro
            110                 115                 120

Val Leu Thr Cys Gly Pro Ala Ser Phe Gln Cys Asn Ser Ser Thr Cys
125                 130                 135

Ile Pro Gln Leu Trp Ala Cys Asp Asn Asp Pro Asp Cys Glu Asp Gly
140                 145                 150                 155

Ser Asp Glu Trp Pro Gln Arg Cys Arg Gly Leu Tyr Val Phe Gln Gly
                160                 165                 170

Asp Ser Ser Pro Cys Ser Ala Phe Glu Phe His Cys Leu Ser Gly Glu
            175                 180                 185

Cys Ile His Ser Ser Trp Arg Cys Asp Gly Gly Pro Asp Cys Lys Asp
        190                 195                 200

Lys Ser Asp Glu Glu Asn Cys Ala Val Ala Thr Cys Arg Pro Asp Glu
205                 210                 215

Phe Gln Cys Ser Asp Gly Asn Cys Ile His Gly Ser Arg Gln Cys Asp
220                 225                 230                 235

Arg Glu Tyr Asp Cys Lys Asp Met Ser Asp Glu Val Gly Cys Val Asn
                240                 245                 250

Val Thr Leu Cys Glu Gly Pro Asn Lys Phe Lys Cys His Ser Gly Glu
            255                 260                 265

Cys Ile Thr Leu Asp Lys Val Cys Asn Met Ala Arg Asp Cys Arg Asp
        270                 275                 280

Trp Ser Asp Glu Pro Ile Lys Glu Cys Gly Thr Asn Glu Cys Leu Asp
285                 290                 295

Asn Asn Gly Gly Cys Ser His Val Cys Asn Asp Leu Lys Ile Gly Tyr
300                 305                 310                 315

Glu Cys Leu Cys Pro Asp Gly Phe Gln Leu Val Ala Gln Arg Arg Cys
                320                 325                 330

Glu Asp Ile Asp Glu Cys Gln Asp Pro Asp Thr Cys Ser Gln Leu Cys
            335                 340                 345

Val Asn Leu Glu Gly Gly Tyr Lys Cys Gln Cys Glu Glu Gly Phe Gln
        350                 355                 360

Leu Asp Pro His Thr Lys Ala Cys Lys Ala Val Gly Ser Ile Ala Tyr
365                 370                 375

Leu Phe Phe Thr Asn Arg His Glu Val Arg Lys Met Thr Leu Asp Arg
380                 385                 390                 395

Ser Glu Tyr Thr Ser Leu Ile Pro Asn Leu Arg Asn Val Val Ala Leu
                400                 405                 410

Asp Thr Glu Val Ala Ser Asn Arg Ile Tyr Trp Ser Asp Leu Ser Gln
            415                 420                 425

Arg Met Ile Cys Ser Thr Gln Leu Asp Arg Ala His Gly Val Ser Ser
        430                 435                 440

Tyr Asp Thr Val Ile Ser Arg Asp Ile Gln Ala Pro Asp Gly Leu Ala
445                 450                 455

Val Asp Trp Ile His Ser Asn Ile Tyr Trp Thr Asp Ser Val Leu Gly
460                 465                 470                 475
```

```
Thr Val Ser Val Ala Asp Thr Lys Gly Val Lys Arg Lys Thr Leu Phe
                480                 485                 490

Arg Glu Asn Gly Ser Lys Pro Arg Ala Ile Val Val Asp Pro Val His
            495                 500                 505

Gly Phe Met Tyr Trp Thr Asp Trp Gly Thr Pro Ala Lys Ile Lys Lys
        510                 515                 520

Gly Gly Leu Asn Gly Val Asp Ile Tyr Ser Leu Val Thr Glu Asn Ile
525                 530                 535

Gln Trp Pro Asn Gly Ile Thr Leu Asp Leu Leu Ser Gly Arg Leu Tyr
540                 545                 550                 555

Trp Val Asp Ser Lys Leu His Ser Ile Ser Ser Ile Asp Val Asn Gly
                560                 565                 570

Gly Asn Arg Lys Thr Ile Leu Glu Asp Glu Lys Arg Leu Ala His Pro
                575                 580                 585

Phe Ser Leu Ala Val Phe Glu Asp Lys Val Phe Trp Thr Asp Ile Ile
            590                 595                 600

Asn Glu Ala Ile Phe Ser Ala Asn Arg Leu Thr Gly Ser Asp Val Asn
        605                 610                 615

Leu Leu Ala Glu Asn Leu Leu Ser Pro Glu Asp Met Val Leu Phe His
620                 625                 630                 635

Asn Leu Thr Gln Pro Arg Gly Val Asn Trp Cys Glu Arg Thr Thr Leu
                640                 645                 650

Ser Asn Gly Gly Cys Gln Tyr Leu Cys Leu Pro Ala Pro Gln Ile Asn
                655                 660                 665

Pro His Ser Pro Lys Phe Thr Cys Ala Cys Pro Asp Gly Met Leu Leu
            670                 675                 680

Ala Arg Asp Met Arg Ser Cys Leu Thr Glu Ala Glu Ala Ala Val Ala
        685                 690                 695

Thr Gln Glu Thr Ser Thr Val Arg Leu Lys Val Ser Ser Thr Ala Val
700                 705                 710                 715

Arg Thr Gln His Thr Thr Thr Arg Pro Val Pro Asp Thr Ser Arg Leu
                720                 725                 730

Pro Gly Ala Thr Pro Gly Leu Thr Thr Val Glu Ile Val Thr Met Ser
                735                 740                 745

His Gln Ala Leu Gly Asp Val Ala Gly Arg Gly Asn Glu Lys Lys Pro
            750                 755                 760

Ser Ser Val Arg Ala Leu Ser Ile Val Leu Pro Ile Val Leu Leu Val
        765                 770                 775

Phe Leu Cys Leu Gly Val Phe Leu Leu Trp Lys Asn Trp Arg Leu Lys
780                 785                 790                 795

Asn Ile Asn Ser Ile Asn Phe Asp Asn Pro Val Tyr Gln Lys Thr Thr
                800                 805                 810

Glu Asp Glu Val His Ile Cys His Asn Gln Asp Gly Tyr Ser Tyr Pro
            815                 820                 825

Ser Arg Gln Met Val Ser Leu Glu Asp Asp Val Ala
        830                 835

(2) INFORMATION FOR SEQ ID NO:5:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide
```

-continued (xi) SEQUENCE DESCRIPTION: SEQ ID NO:5:

Asp Arg Xaa Glu Arg Asn Glu Phe Gln Xaa Gln Asp Gly Lys Xaa Ile
1               5                   10                  15

(2) INFORMATION FOR SEQ ID NO:6:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Asp Arg Cys Glu Arg Asn Glu Phe Gln Cys Gln Asp Gly Lys Cys Ile
1               5                   10                  15